US012409232B2

(12) United States Patent
Miyata et al.

(10) Patent No.: US 12,409,232 B2
(45) Date of Patent: Sep. 9, 2025

(54) TEMPERATURE-RESPONSIVE DRUG/POLYMER COMPOUND AND APPLICATION OF COMPOUND TO DRUG DELIVERY

(71) Applicant: The University of Tokyo, Tokyo (JP)

(72) Inventors: Kanjiro Miyata, Tokyo (JP); Beob Soo Kim, Tokyo (JP); Shigehito Osawa, Tokyo (JP); Mitsuru Naito, Tokyo (JP); Hiroyuki Chaya, Tokyo (JP)

(73) Assignee: The University of Tokyo, Tokyo (JP)

( * ) Notice: Subject to any disclaimer, the term of this patent is extended or adjusted under 35 U.S.C. 154(b) by 899 days.

(21) Appl. No.: 17/628,676

(22) PCT Filed: Jul. 27, 2020

(86) PCT No.: PCT/JP2020/028698
§ 371 (c)(1),
(2) Date: Jun. 29, 2022

(87) PCT Pub. No.: WO2021/020342
PCT Pub. Date: Feb. 4, 2021

(65) Prior Publication Data
US 2022/0331439 A1    Oct. 20, 2022

Related U.S. Application Data

(60) Provisional application No. 62/878,970, filed on Jul. 26, 2019.

(51) Int. Cl.
*A61K 47/61* (2017.01)
*A61K 9/107* (2006.01)
(Continued)

(52) U.S. Cl.
CPC ............ *A61K 47/61* (2017.08); *A61K 9/1075* (2013.01); *A61K 47/545* (2017.08); *A61K 47/55* (2017.08)

(58) Field of Classification Search
CPC ...... A61K 47/61; A61K 9/1075; A61K 38/00; A61K 31/7088
See application file for complete search history.

(56) References Cited

FOREIGN PATENT DOCUMENTS

JP    2019-38787 A   *  3/2019
JP    2019038787 A       3/2019

OTHER PUBLICATIONS

Keiji Itaka et al., "Gene transfer into the lung by nanocarriers that have bothfunctionality and inflammation control", Preprints of the 33rd Annual Meeting of the Japanese Society for Biomaterials, Dec. 31, 2011, p. 215.

(Continued)

*Primary Examiner* — Carlos A Azpuru
(74) *Attorney, Agent, or Firm* — J-TEK LAW PLLC; Jeffrey D. Tekanic; Scott T. Wakeman

(57) ABSTRACT

A drug-polymer conjugate having thermoresponsiveness includes at least one drug conjugated to at least one end portion of at least one thermoresponsive polymer segment having a lower critical solution temperature. The drug-polymer conjugate is capable of forming a micellular aggregate in an aqueous medium at temperatures equal to or above the lower critical solution temperature. The drug-polymer conjugate or the micellular aggregate thereof may be administered to and absorbed in the lungs.

20 Claims, 16 Drawing Sheets

Specification includes a Sequence Listing.

(51) Int. Cl.
A61K 47/54 (2017.01)
A61K 47/55 (2017.01)

(56) References Cited

OTHER PUBLICATIONS

Masamichi Nakayama et al., "Intelligent biomaterials and DDS", Journal of the clinical and experimental medicine, Aug. 2004, vol. 210, No. 9, pp. 721-725.
A. Christy Hunter, "Molecular hurdles in polyfectin design and mechanistic background to polycation induced cytotoxicity", Advanced Drug Delivery Reviews, Sep. 2006, pp. 1523-1531, published by Elsevier, Amsterdam, The Netherlands.
A. Nemmar, et al., "Passage of Intratracheally Instilled Ultrafine Particles from the Lung into the Systemic Circulation in Hamster", American Journal of Respiratory and Critical Care Medicine, 2001, pp. 1665-1668, vol. 164, Laboratory of Pneumology (Lung Toxicology), Laboratory of Radiopharmaceutical Chemistry, and Center for Molecular and Vascular Biology, Leuven, Belgium.
Breit P. Monia, et al., "Antitumor activity of a phosphorothioate antisense oligodeoxynucleotide targeted against C-raf kinase", Nature Medicine, pp. 668-675, vol. 2, No. 6, Jun. 1996, Nature Publishing Group, New York, NY, U.S.A.
Claes Wahkestedt et al., "Potent and nontoxic antisense oligonucleotides containing locked nucleic acids", May 9, 2000, pp. 5633-5638, vol. 97. No. 10, The Proceedings of the National Academy of Sciences, Washington, DC, U.S.A.
Dagmar Fischer et al., "In vitro cytotoxicity testing of polycations: influence of polymer structure on cell viability andhemolysis", Biomaterials, Sep. 2002, pp. 1121-1131, published by Elsevier, Amsterdam, The Netherlands.
E. Van Rooij et al., "MicroRNA therapeutics for cardiovascular disease: opportunities and obstacles", Nature Reviews Drug Discovery, Nov. 2012, pp. 1-29, Nature Publishing Group, London, UK.
English translation of International Preliminary Report on Patentability issued in parent International application No. PCT/JP2020/028698.
English translation of International Search Report issued in parent International application No. PCT/JP2020/028698.
Hak Soo Choi, et al., "Rapid Translocation of Nanoparticles from the Lung Airspaces to the Body", National Institute of Health, Dec. 2010, pp. 1-11, NIH Public Access, U.S.A.
Hiroyasu Takemoto, et al., "Accelerated Polymer-Polymer Click Conjugation by Freeze-Thaw Treatment", Bioconjugate Chemistry, Jul. 2012, pp. 1503-1506, ACS Publications, Washington, D.C., U.S.A.
Zhonglan Tan et al., "Non-Cross-Linking Aggregation of DNA-Carrying Polymer Micelles Triggered by Duplex Formation", Langmuir, Aug. 2018, pp. 14899-14910, vol. 34, ACS Publications, Washington D.C., U.S.A.
Horacio Cabral, et al., "Block Copolymer Micelles in Nanomedicine Applications", Chemical Reviews, Jun. 2018, pp. 6844-6892, ACS Publications, Washington, DC, U.S.A.
Huan Liu, et al., "Long noncoding RNA TUG1 is a diagnostic factor in lung adenocarcinoma and suppresses apoptosis via epigenetic silencing of BAX", Oncotarget, Oct. 2017, pp. 101899-101910, vol. 8.
Jing Huang, et al., "Effects of Nanoparticle Size on Cellular Uptake and Liver MRI with PVP-Coated Iron Oxide Nanoparticles", National Institute of Health, Dec. 2011, pp. 1-22, NIH Public Access, U.S.A.
Joon-Sik Park, et al., "Comprehensive and Accurate Control of Thermosensitivity of Poly(2-alkyl-2-oxazoline)s via Well-Defined Gradient or Random Copolymerization", Macromolecules, 2007, pp. 3599-3609, ACS Publications, Washington, D.C., U.S.A.
Kees Fluiter et al., "In vivo tumor growth inhibition and biodistribution studies of locked nucleic acid (LNA) antisense oligonucleotides", Nucleic Acids Research, 2003, pp. 953-962, vol. 31, No. 3, Oxford University Press, U.K.

Keisuke Katsushima, et al., "Targeting the Notch-regulated noncoding RNA TUG1 for glioma treatment", Dec. 2016, pp. 1-14, Published by Nature Communications, London, U.K.
Laura J. Smithson, et al., "Microglial/Macrophage Cells in Mammalian Olfactory Nerve Fascicles", Journal of Neuroscience Research, Oct. 2009, pp. 858-865, Published by Wiley-Liss, Inc., New Jersey, U.S.A.
Lei Peng, et al., "Development of a Novel Orthotopic Non-small Cell Lung Cancer Model and Therapeutic Benefit of 2'-(2-bromohexadecanoyl)-Docetaxel Conjugate Nanoparticles", Nanomedicine, National Institute of Public Health, Oct. 2014, vol. 10(7), pp. 1497-1506.
Liang Zhao, et al., "The Lncrna-TUG1/EZH2 Axis Promotes Pancreatic Cancer Cell Proliferation, Migration and EMT Phenotype Formation Through Sponging Mir-382", Cellular Physiology and Biochemistry, Aug. 2017, pp. 2145-2158, Published by S. Karger AG, Basel, Switzerland.
Olga B. Garbuzenko, et al., "Intratracheal Versus Intravenous Liposomal Delivery of siRNA, Antisense Oligonucleotides and Anticancer Drug", Pharmaceutical Research, Feb. 2009, pp. 382-394, vol. 26, No. 2.
Per Rigler, et al., "Encapsulation of Fluorescent Molecules by Functionalized Polymeric Nanocontainers: Investigation by Confocal Fluorescence Imaging and Fluorescence Correlation Spectroscopy", Journal of the American Chemical Society, 2006, pp. 367-373, vol. 128, ACS publications, Washington, DC, U.S.A.
Rafael A. Madero-Visbal, et al., "Bioluminescence imaging correlates with tumor progression in an orthotopic mouse model of lung cancer", Surgical Oncology, 2012, vol. 21, pp. 23-29, Published by Elsevier, Amsterdam, The Netherlands.
Richard Hoogenboom, et al., "Tuning the LCST of poly(2-oxazoline)s by varying composition and molecular weight: alternatives to poly(N-isopropylacrylamide)?", Chemical Communications, The Royal Society of Chemistry, 2008, pp. 5758-5760, Cambridge. U.K.
Robert C. Lindenschmidt, et al.. "Intratracheal versus Intravenous Administration of Bleomycin in Mice: Acute Effects", Toxicology and Applied Pharmacology, 1986, pp. 69-77, Academic Press. Inc., Cambridge, Massachussetts, U.S.A.
S. Moein Mopghimi,et al.,"A Two-Stage Poly(ethylenimine)-Mediated Cytotoxicity: Implications for Gene Transfer/Therapy", Molecular Therapy, Jun. 2005, pp. 990-995, vol. 11, No. 6, The American Society of Gene Therapy.
Shigehito Osawa, et al., "Polyplex Micelles with Double-Protective Compartments of Hydrophilic Shell and Thermoswitchable Palisade of Poly(oxazoline)-Based Block Copolymers for Promoted Gene Transfection", Biomacromolecules, 2015, pp. 354-361, ACS Publications, Washington, D.C., U.S.A.
Yasunori Uemura, et al., "The intratracheal administration of locked nucleic acid containing antisense oligonucleotides induced gene silencing and an immune-stimulatory effect in the murine lung", "Knock down and immune-stimulatory effect of LNA-ASOs in the lung", PLOS One, Nov. 2017, pp. 1-14, San Francisco, California, U.S.A.
Sterghios A Moschos et al., "Uptake, Efficacy, and Systemic Distribution of Naked, Inhaled Short Interfering RNA (siRNA) and Locked Nucleic Acid (LNA) Antisense", Molecular Therapy, The American Society of Gene & Cell Therapy, 2011, pp. 2163-2168, vol. 19.
Kue-hai Liang et al., "Identification and characterization of intracellular proteins that bind oligonucleotides with phosphorothioate linkages", Nucleic Acids Research, 2015, pp. 2927-2945, vol. 43, No. 5, Oxford University Press, U.K.
Sulin Zhang, et al., "Size-Dependent Endocytosis of Nanoparticles", Adv Mater., National Institute of Health, Jul. 2009, pp. 1-14, NIH Public Access, U.S.A.
Sumiyo Watanabe, et al., "In vivo rendezvous of small nucleic acid drugs with charge-matched block catiomers to target cancers", Nature Communications, Apr. 24, 2019, pp. 1-13.
Tanima Bose, et al., "Overview of nano-drugs characteristics for clinical application: the journey from the entry to the exit point", Journal of Nanoparticle Research, Jul. 2014, pp. 1-25, Springer Publishing, New York, U.S.A.

(56) References Cited

OTHER PUBLICATIONS

Wen Jiang, et al., "Nanoparticle-mediated cellular response is size-dependent", Nature Nanotechnology, Mar. 2008, vol. 3, pp. 145-150, Published by Nature Publishing Group, London, U.K.
Office Action from the Japanese Patent Office dated Jun. 4, 2024, in related Japanese patent application No. 2021-535327, and machine translation thereof.

* cited by examiner (a)  (b)

LIVER  SPLEEN KIDNEY HEART LUNG TUMOR

TEMPERATURE-RESPONSIVE DRUG/POLYMER COMPOUND AND APPLICATION OF COMPOUND TO DRUG DELIVERY

CROSS-REFERENCE

This application is the US national stage of International Patent Application No. PCT/JP2020/028698 filed on Jul. 27, 2020, which claims priority to U.S. Provisional Patent Application No. 62/878,970 filed on Jul. 26, 2019.

REFERENCE TO SEQUENCE LISTING FILED VIA EFS-WEB

The present application contains a Sequence Listing that has been electronically submitted in ASCII text format via EFS-Web and is incorporated herein by reference in its entirety. The sequence listing is identified on the electronically-filed text file as follows:

| File Name | Date of Creation | Size (KB) |
|---|---|---|
| 5_TKU20162PCT_sequence listing.txt | Apr. 6, 2022 | 2 |

TECHNICAL FIELD

The present invention relates to a drug-polymer conjugate having thermoresponsiveness and application of the conjugate to drug delivery. More specifically, the present invention relates to a drug-polymer conjugate having thermoresponsiveness, and a micellar aggregate including the drug-polymer conjugate and a use or production method thereof.

BACKGROUND ART

Chemically modified antisense oligonucleotides (ASOs) containing phosphorothioate linkages and bridged nucleic acids (LNAs or BNAs) are promising therapeutic candidates for a variety of intractable diseases, including cancer, because of their high tolerability against enzymatic degradation and high affinity to target RNAs, which can induce gene knockdown.

In addition, intratracheal administration is a promising method of delivering and concentrating a drug into the lungs without distribution to other tissues or organs.

However, there is a report that, when inhaled alone by a mouse through the trachea, a chemically modified antisense oligonucleotide (naked ASO) accumulates in the liver and kidneys to be unable to exhibit significant gene knockdown in the lungs (Non Patent Literature 1).

CITATION LIST

Patent Literature

[NPL 1] Molecular Therapy, vol. 19, No. 12, 2163-2168, December 2011

SUMMARY OF INVENTION

The present invention has been made in order to solve the above-mentioned problem, and a primary object of the present invention is to provide a method of efficiently delivering a drug to the lungs.

According to one aspect of the present invention, there is provided a drug-polymer conjugate having thermoresponsiveness, including: a thermoresponsive polymer segment; and a drug conjugated to an end of the thermoresponsive polymer segment, the drug-polymer conjugate having a lower critical solution temperature.

In one embodiment, the thermoresponsive polymer segment has a molecular weight of $1.0 \times 10^4$ or more.

In one embodiment, the lower critical solution temperature falls within a range of from 0° C. to 35° C.

In one embodiment, the drug is at least one kind selected from a nucleic acid and a peptide.

In one embodiment, the drug is at least one kind of nucleic acid selected from an antisense oligonucleotide, siRNA, miRNA, a hetero nucleic acid, a CpG oligonucleotide, a nucleic acid aptamer, and a decoy nucleic acid.

According to another aspect of the present invention, there is provided a micellar aggregate, including the drug-polymer conjugate, wherein the thermoresponsive polymer segment is arranged inward, and the drug is arranged outward.

In one embodiment, the micellar aggregate has a hydrodynamic diameter of from 10 nm to 300 nm.

According to yet another aspect of the present invention, there is provided a pharmaceutical composition, including the drug-polymer conjugate, or the micellar aggregate.

In one embodiment, the pharmaceutical composition is an inhalant.

According to yet another aspect of the present invention, there is provided a method of delivering the pharmaceutical composition to a lung, including nasally administering or intratracheally administering the pharmaceutical composition to an individual in need of intervention.

According to yet another aspect of the present invention, there is provided a method of producing the micellar aggregate, including: dissolving the drug-polymer conjugate in an aqueous medium at a temperature equal to or lower than the lower critical solution temperature to obtain a drug-polymer conjugate solution; and heating the drug-polymer conjugate solution to a temperature higher than the lower critical solution temperature to aggregate the drug-polymer conjugate.

In the present invention, the drug-polymer conjugate having thermoresponsiveness can be used to form an aggregate of the conjugate in an aqueous medium in a temperature-dependent manner. The aggregate is pulmonarily absorbed through nasal administration or intratracheal administration, and can suitably stay in a lung tissue, thereby enabling efficient drug delivery to the lungs. In addition, a related-art drug delivery system using a cationic substance, such as a cationic lipid or a cationic polymer, is feared to exhibit cytotoxicity due to, for example, interactions with cell membranes and mitochondrial membranes, and non-specific adsorption with proteins, but the drug-polymer conjugate of the present invention enables the formation of a micellar aggregate without using any cationic material.

DESCRIPTION OF EMBODIMENTS

Preferred embodiments of the present invention are described below, but the present invention is not limited to these embodiments. In addition, the embodiments may be appropriately combined with each other.

Figure 1A:
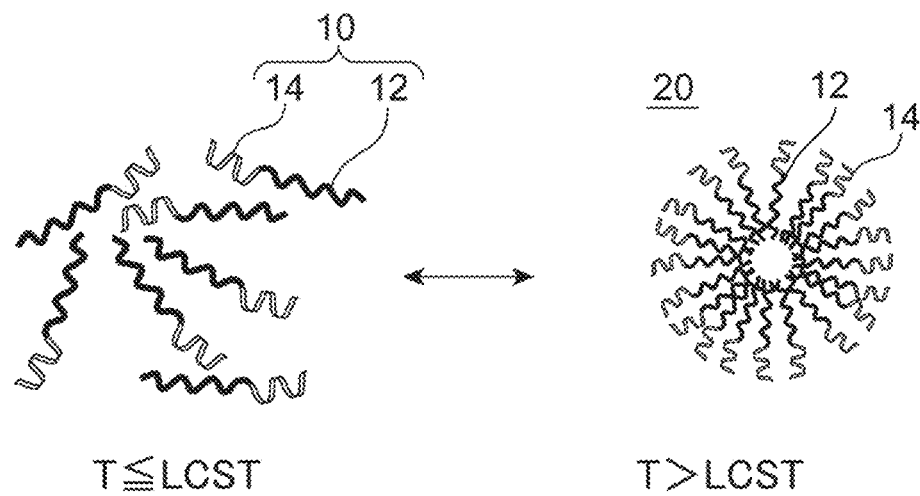
FIG. 1A is a schematic view for illustrating the outline of one embodiment of the present invention.
Figure 1A:
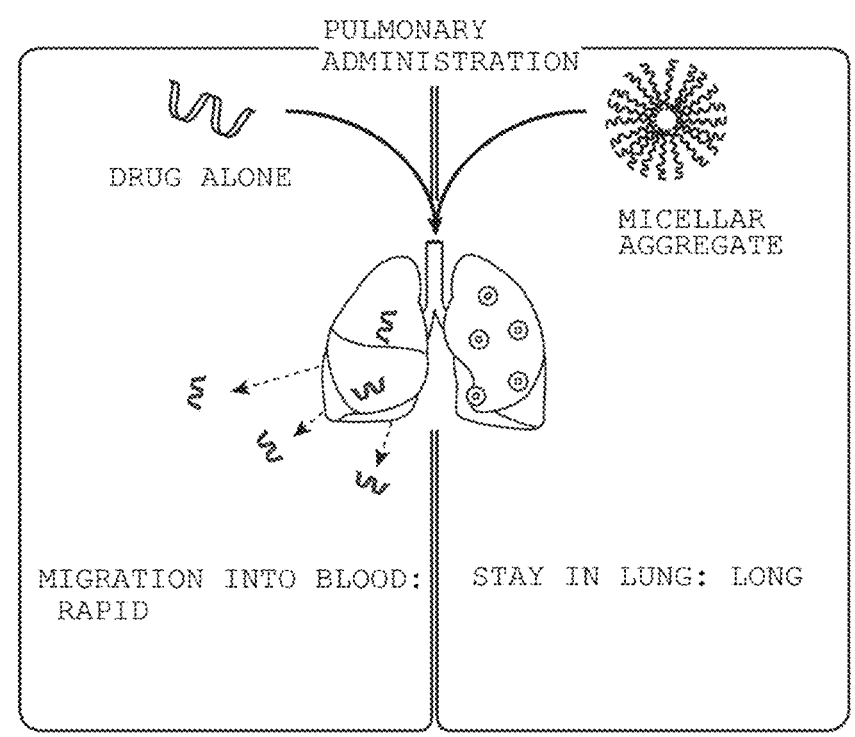

FIG. 1A is a schematic view for illustrating the outline of one embodiment of the present invention. A drug-polymer conjugate 10 having thermoresponsiveness exemplified in FIG. 1A includes a thermoresponsive polymer segment 12 and a drug 14 conjugated to one end of the thermoresponsive polymer segment 12, and has a lower critical solution temperature (hereinafter "LCST"). Specifically, the drug-polymer conjugate 10 having thermoresponsiveness exhibits such a reversible phase transition as to be hydrated to become soluble in water under a temperature condition equal to or lower than the LCST, but to be dehydrated to become insoluble (poorly soluble) in water under a temperature condition higher than the LCST. Accordingly, in an aqueous medium, the drug-polymer conjugate 10 is in a state of being hydrated and dissolved at a temperature equal to or lower than the LCST, but is dehydrated and aggregated through an intermolecular and/or intramolecular hydrophobic interaction at a temperature higher than the LCST, thereby being able to form a micellar aggregate 20 with the thermoresponsive polymer segment 12 portion arranged inward and the drug 14 portion arranged outward. The micellar aggregate 20 can be pulmonarily absorbed in an efficient manner, and can also satisfactorily stay in a lung tissue through suppression of migration into blood after pulmonary absorption as compared to the case of administration of the drug 14 alone, thereby enabling efficient drug delivery to the lungs.

A. Drug-Polymer Conjugate

The drug-polymer conjugate according to the embodiment of the present invention is a thermoresponsive drug-polymer conjugate including a thermoresponsive polymer segment and a drug conjugated to an end of the thermoresponsive polymer segment, and having a lower critical solution temperature (LCST).

The drug-polymer conjugate 10 illustrated in FIG. 1A includes the thermoresponsive polymer segment 12 and the drug 14 conjugated to one end of the thermoresponsive polymer segment 12. The drug-polymer conjugate 10 according to this embodiment may be represented by the formula: A-B (where A represents the thermoresponsive polymer segment, and B represents the drug). As described above, the drug-polymer conjugate 10 according to this embodiment can form the micellar aggregate 20 aggregated in such a manner that the thermoresponsive polymer segment 12 is directed inward and the drug 14 is directed outward in an aqueous medium at a temperature higher than the LCST.

The drug-polymer conjugate according to the embodiment of the present invention is not limited to the configuration illustrated in FIG. 1A as long as the drug-polymer conjugate has an LCST and can form the micellar aggregate with the thermoresponsive polymer segment portion arranged inward and the drug portion arranged outward in an aqueous medium at a temperature higher than the LCST.

Figure 1B:
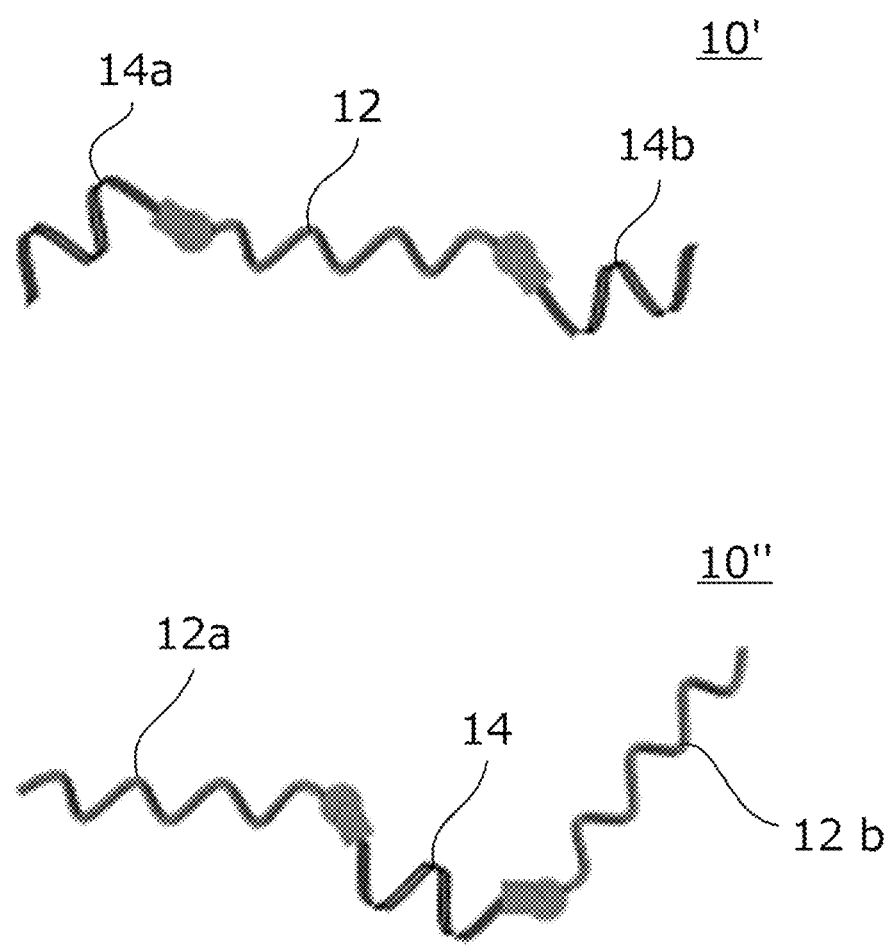
FIG. 1B is a schematic view for illustrating modified examples of the drug-polymer conjugate.

For example, modified examples of the drug-polymer conjugate according to the embodiment of the present invention are illustrated in FIG. 1B. A drug-polymer conjugate 10' illustrated in FIG. 1B includes the thermoresponsive polymer segment 12, a first drug 14a conjugated to one end of the thermoresponsive polymer segment, and a second drug 14b conjugated to the other end. The drug-polymer conjugate 10' according to this embodiment may be represented by the formula: $B_1$-A-$B_2$ (where A represents the thermoresponsive polymer segment, $B_1$ represents the first drug, and $B_2$ represents the second drug). The first drug and the second drug may be the same as or different from each other as long as the effects of the present invention are obtained.

In addition, a drug-polymer conjugate 10" illustrated in FIG. 1B includes the drug 14, a first thermoresponsive polymer segment 12a conjugated to one end of the drug 14, and a second thermoresponsive polymer segment 12b conjugated to the other end. The drug-polymer conjugate 10" according to this embodiment may be represented by the formula: $A_1$-B-$A_2$ (where $A_1$ represents the first thermoresponsive polymer segment, $A_2$ represents the second thermoresponsive polymer segment, and B represents the drug). The first thermoresponsive polymer segment and the second thermoresponsive polymer segment may have the same configuration or different configurations as long as the effects of the present invention are obtained.

The drug-polymer conjugate according to the embodiment of the present invention enables a micellar aggregate to be formed in a self-assembling manner with the polymer segment portion arranged inward and the drug portion arranged outward in an aqueous medium at a temperature higher than the LCST. Accordingly, the micellar aggregate can be prepared easily and in a completely aqueous system without using an organic solvent, such as an alcohol, an ester, or a ketone, by dissolving the drug-polymer conjugate in an aqueous medium to prepare a drug-polymer conjugate solution, and storing the drug-polymer conjugate solution as required, at a temperature equal to or lower than the LCST, and heating the drug-polymer conjugate solution to a temperature higher than the LCST at the time of use.

In one embodiment, the drug-polymer conjugate has an LCST within the range of, for example, from 0° C. to 40° C., preferably from 0° C. to 35° C., more preferably from 0° C. to 30° C. (e.g., from 0° C. to 25° C., from 0° C. to 20° C., or from 0° C. to 15° C.) According to this embodiment, after a micellar aggregate has been prepared at a temperature higher than the LCST, the resultant micellar aggregate may be administered to an individual. The LCST may be generally determined by the turbidity or scattered light intensity measurement of a sample solution prepared at a concentration sufficient for aggregate formation (e.g., equal to or higher than a critical association concentration). That is, in the case of determining the LCST of the drug-polymer conjugate, the following temperature may be determined as the LCST: a temperature at which a rapid increase in turbidity or scattered light intensity starts when a drug-polymer conjugate solution prepared at low temperature is measured for its turbidity or scattered light intensity while being increased in temperature.

In one embodiment, the drug-polymer conjugate has an LCST within the range of from an administration subject individual's body temperature–5° C. to the administration subject individual's body temperature. According to this embodiment, the drug-polymer conjugate solution can be administered to the individual to form the micellar aggregate in the body of the individual.

In one embodiment, the drug-polymer conjugate is in a hydrated state in water at 4° C. or less or 10° C. or less, thereby being soluble in the water, but is in a dehydrated state in water at 20° C. or more, 25° C. or more, or 30° C. or more, thereby being able to undergo micellar aggregation at a concentration equal to or higher than a critical micelle concentration (CMC) at such water temperature.

The LCST of the drug-polymer conjugate may correspond to the LCST of the thermoresponsive polymer serving as the thermoresponsive polymer segment, and hence a drug-polymer conjugate having a desired LCST may be obtained by adjusting the LCST of the thermoresponsive polymer.

A-1. Thermoresponsive Polymer Segment

Any appropriate thermoresponsive polymer may be used as the thermoresponsive polymer serving as the thermoresponsive polymer segment as long as a desired LCST can be imparted to the drug-polymer conjugate. In one embodiment, the thermoresponsive polymer has an LCST within the range of, for example, from 0° C. to 40° C., preferably from 0° C. to 35° C., more preferably from 0° C. to 30° C. (e.g., from 0° C. to 25° C., from 0° C. to 20° C., or from 0° C. to 15° C.). When the thermoresponsive polymer having an LCST within such ranges is used, the drug-polymer conjugate having an LCST within the above-mentioned desired ranges can be suitably obtained.

A specific example of the thermoresponsive polymer is a thermoresponsive polymer containing at least one kind of repeating unit selected from:

(a) an oxazoline-based repeating unit represented by the following formula (I) (in the formula (I), $R^1$ represents a methyl group, an ethyl group, a n-propyl group, an isopropyl group, or a n-butyl group, preferably a n-propyl group, an isopropyl group, or a n-butyl group);

(b) an N-alkylacrylamide-based repeating unit represented by the following formula (II) (in the formula (II), $R^2$ represents a methyl group, an ethyl group, a n-propyl group, an isopropyl group, a n-butyl group, or a t-butyl group, preferably a n-propyl group, an isopropyl group, a n-butyl group, or a t-butyl group);

(c) an N-vinylalkylamide-based repeating unit represented by the following formula (III) (in the formula (III), $R^3$ represents a methyl group, an ethyl group, a n-propyl group, an isopropyl group, a n-butyl group, or a t-butyl group, preferably a n-propyl group or an isopropyl group); and (d) a vinyl alkyl ether-based repeating unit represented by the following formula (IV) (in the formula (IV), $R^4$ represents a methyl group, an ethyl group, a n-propyl group, or an isopropyl group, preferably a methyl group or an ethyl group). The thermoresponsive polymer may contain only one kind or two or more kinds of the repeating units represented by the following formulae (I) to (IV). In addition, the thermoresponsive polymer may contain a repeating unit other than the repeating units represented by the formulae (I) to (IV) to the extent that the effects of the present invention are obtained.

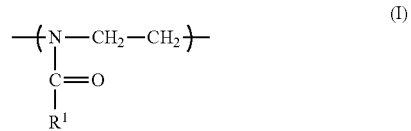

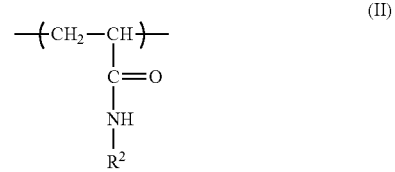

-continued

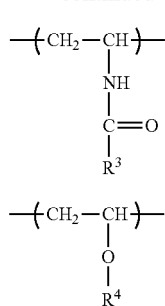

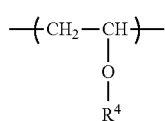

A poly(oxazoline)-based thermoresponsive polymer containing an oxazoline-based repeating unit is preferred because its polymerization degree is easy to control and a polymer having high monodispersibility can be easily obtained. Preferred specific examples of the poly(oxazoline)-based thermoresponsive polymer may include poly(2-n-propyl-2-oxazoline), poly(2-isopropyl-2-oxazoline), and poly(2-n-butyl-2-oxazoline).

The LCST of the thermoresponsive polymer tends to shift to lower temperatures as the carbon chains of $R^1$ to $R^4$ in the repeating units become longer when the polymerization degree remains the same. In addition, the LCST of the thermoresponsive polymer tends to shift to lower temperatures as the polymerization degree becomes larger when the kinds and ratios of the repeating units contained in the polymer remain the same. Accordingly, a thermoresponsive polymer having a desired LCST can be obtained by adjusting the kinds, ratios, and polymerization degrees of the repeating units.

The molecular weight (i.e., mass (Da)) of the thermoresponsive polymer is preferably $1.0 \times 10^4$ or more, more preferably $2.0 \times 10^4$ or more, still more preferably $3.0 \times 10^4$ or more. The upper limit of the molecular weight of the thermoresponsive polymer is not particularly limited, but may be, for example, $2.0 \times 10^5$, or for example, $1.0 \times 10^5$. When the molecular weight of the thermoresponsive polymer falls within the ranges, the thermoresponsive polymer provides a sufficient hydrophobic interaction when insolubilized, and hence is favorable to the formation of a micellar aggregate. In addition, when the molecular weight falls within the ranges, a thermoresponsive polymer having an LCST within the above-mentioned desired ranges (consequently a drug-polymer conjugate having an LCST within the above-mentioned desired ranges) can be easily obtained.

As required, a hydrophobic group may be introduced into the end of the thermoresponsive polymer segment to which the drug is not conjugated. Examples of such hydrophobic group include an alkyl group or alkoxy group having 1 to 8 carbon atoms, and an aryl group, aralkyl group, aryloxy group, or aralkyloxy group having 6 to 12 carbon atoms.

A-2. Drug

It is preferred to use, as the drug, a drug showing higher hydrophilicity than the thermoresponsive polymer segment dehydrated in an aqueous medium. When such drug is used, a micellar aggregate in which the thermoresponsive polymer segment is arranged inward to form a hydrophobic core, and in which the drug is arranged outward can be easily obtained in an aqueous medium at a temperature higher than the LCST. In addition, when the drug is neutral or anionic, the surface of the micellar aggregate is neutral or negatively charged. Accordingly, secondary aggregation is suppressed, and besides, an undesired interaction with, for example, a biological membrane or a protein, which occurs in the case of positive charge, can be prevented.

The molecular weight (i.e., mass (Da)) of the drug is preferably $1.0 \times 10^3$ or more, more preferably $2.0 \times 10^3$ or more, still more preferably $3.0 \times 10^3$ or more. The upper limit of the molecular weight (i.e., weight (Da)) of the drug is not particularly limited, but may be, for example, $1.0 \times 10^5$, or for example, $5.0 \times 10^4$. When a hydrophilic polymer is used as the drug, a micellar aggregate having a surface covered with the hydrophilic polymer is obtained, and hence a reduction in inflammatory property and satisfactory absorption into the lungs are expected.

In one embodiment, the drug is a nucleic acid. The nucleic acid means a poly- or oligonucleotide including, as basic units, nucleotides each of which is formed of a purine or pyrimidine base, a pentose, and phosphoric acid, and examples thereof may include oligo- or poly-double-stranded RNA, oligo- or poly-double-stranded DNA, oligo- or poly-single-stranded DNA, and oligo- or poly-single-stranded RNA. In addition, the examples also include an oligo- or poly-double-stranded nucleic acid and an oligo- or poly-single-stranded nucleic acid in each of which RNA and DNA exist in a mixed state in the same strand. The nucleotides contained in the nucleic acid may each be of a natural type or of a chemically modified non-natural type, and may each have added thereto an amino group, a thiol group, a fluorescent compound, or any other molecule.

The base length of the nucleic acid may be, for example, from 5 to 150, preferably from 10 to 100, more preferably from 12 to 50.

In consideration of the function or action of the nucleic acid, examples thereof include an antisense oligonucleotide, siRNA, miRNA, a hetero double-stranded nucleic acid, a CpG oligodeoxynucleotide, a nucleic acid aptamer, and a decoy nucleic acid.

In one embodiment, the drug is a peptide. The peptide is not limited as long as the peptide has physiological activity as a drug, and may be appropriately selected in accordance with purposes. The peptide may contain only natural amino acids, or may contain a non-natural amino acid.

The molecular weight (i.e., mass (Da)) of the peptide may be, for example, from $1.0 \times 10^3$ to $1.0 \times 10^4$, preferably from $1.0 \times 10^3$ to $5.0 \times 10^3$.

A-3. Production Method

The drug-polymer conjugate is typically obtained by conjugating the drug to an end of the thermoresponsive polymer. For example, the drug-polymer conjugate represented by the formula: A-B may be obtained by a method including: synthesizing the thermoresponsive polymer through a polymerization reaction; introducing a first functional group into one end of the thermoresponsive polymer to obtain a thermoresponsive polymer having one end modified with a functional group; preparing a drug having a second functional group capable of reacting with the first functional group; and allowing the first functional group and the second functional group to react with each other to conjugate the thermoresponsive polymer having one end modified with a functional group and the drug to each other.

With regard to the combination of the first functional group and the second functional group, a covalent bond formed through the reaction between these functional groups may be cleavable or poorly cleavable in vivo. Specific examples of the combination include an azide group and an alkyne, a thiol group and a (meth)acryloyl group, a thiol group and a maleimide group, a thiol group and a thiol group, a thiol group and a carboxyl group, a (meth)acryloyl group and a hydroxyl group, a (meth)acryloyl group and an amino group, a carboxyl group and an amino group, a carboxyl group and a hydroxyl group, and an amino group and a hydroxyl group (needless to say, any of the former and the latter among those combinations may serve as the first functional group). The second functional group may be inherent to the drug, or may be artificially introduced.

B. Micellar Aggregate

A micellar aggregate according to an embodiment of the present invention includes the drug-polymer conjugate described in the section A. In the micellar aggregate, the thermoresponsive polymer segment is arranged inward, and the drug is arranged outward.

The micellar aggregate may further include a thermoresponsive polymer in addition to the drug-polymer conjugate described in the section A. When the micellar aggregate further includes the thermoresponsive polymer, the volume of the inward portion (core portion) in the formation of the aggregate can be increased to increase the particle diameter of the micellar aggregate to be obtained. In this case, from the viewpoint of the ease with which the particle diameter is adjusted, it is preferred to use, as the thermoresponsive polymer, a thermoresponsive polymer having the same configuration as the thermoresponsive polymer (segment) included in the drug-polymer conjugate.

The particle diameter (hydrodynamic diameter, $D_H$) of the micellar aggregate may be appropriately set in accordance with purposes. From the viewpoint of suppressing migration from the lungs into the systemic circulation after pulmonary absorption, the particle diameter ($D_H$) is preferably from 10 nm to 300 nm, more preferably from 20 nm to 250 nm, still more preferably from 30 nm to 200 nm, even more preferably from 40 nm to 150 nm. According to the aggregate having such particle diameter, while satisfactory cellular uptake is performed in the lungs, subsequent migration into the systemic circulation is suppressed, and hence the drug can be delivered to the lungs efficiently and locally.

The polydispersity index (PDI) of the micellar aggregate is, for example, 0.6 or less, preferably 0.4 or less, more preferably 0.2 or less, still more preferably 0.15 or less.

The zeta-potential of the micellar aggregate is typically 5 mV or less, preferably 3 mV or less, more preferably 0 mV or less. When the zeta-potential falls within such ranges, a micellar aggregate excellent in stability is obtained, and besides, an undesired interaction with, for example, a biological membrane or a protein can be prevented.

The micellar aggregate is formed in a self-assembling manner by, for example, dissolving the drug-polymer conjugate described in the section A (and the thermoresponsive polymer serving as an optional component) in an aqueous medium at a temperature equal to or lower than the LCST, for example, a temperature lower than the LCST by 10° C. or more, and heating the resultant drug-polymer conjugate solution to a temperature higher than the LCST, preferably a temperature higher than the LCST by 10° C. or more. The aqueous medium may be buffered as required, and for example, HEPES buffer, PBS, or Tris buffer may be used.

The concentration of the drug-polymer conjugate in the drug-polymer conjugate solution is not limited as long as the micellar aggregate is formed, and generally only needs to be a concentration equal to or higher than the critical micelle concentration at the water temperature in the formation of the aggregate. The concentration of the drug-polymer conjugate may be, for example, 10 nM or more, preferably 20 nM or more, more preferably 40 nM or more.

C. Pharmaceutical Composition

A pharmaceutical composition according to an embodiment of the present invention includes the drug-polymer conjugate described in the section A or the micellar aggregate described in the section B. The pharmaceutical composition is preferably aimed at treating or preventing lung diseases, such as cancer, a pleural tumor, pneumonia, pulmonary tuberculosis, pleurisy, bronchial asthma, cystic lung fibrosis, and chronic obstructive pulmonary disease, and germ (e.g., bacterial or viral) infections each of which affects the upper respiratory tract, the lower respiratory tract, or the like, and their accompanying complications such as respiratory failure syndrome. In addition, the pharmaceutical composition according to this embodiment is preferably delivered to the upper respiratory tract (nasal cavity, pharynx, or larynx) or the lower respiratory tract (trachea, bronchi, or lungs) (pulmonarily absorbed) through nasal administration or intratracheal administration. The cancer to be treated or prevented encompasses not only lung cancer with a primary tumor in the lungs, but also cancer that has metastasized to the lungs from any other organ.

The pharmaceutical composition is prepared into any appropriate dosage form in accordance with its administration method. From the viewpoint of nasal administration or intratracheal administration, the dosage form is preferably an inhalant, and specific examples thereof include an inhalable solution, an inhalable aerosol, and an inhalable powder.

The pharmaceutical composition may further include a drug other than the drug in the drug-polymer conjugate in accordance with purposes. In addition, any appropriate additive may be used in accordance with the desired dosage form. The additive only needs to be a pharmaceutically acceptable one, and examples thereof may include an excipient, a diluent, a solubilizing agent, a suspending agent, a tonicity agent, a pH adjuster, a buffer, and a stabilizing agent.

The dose (specifically, dose in terms of the drug) and administration interval of the pharmaceutical composition may be appropriately set in accordance with, for example, the kind and disease stage of a lung disease, and the state of an individual to be subjected to intervention.

D. Delivery Method

According to another aspect of the present invention, there is provided a method of delivering the pharmaceutical composition described in the section C (more specifically, the drug-polymer conjugate described in the section A or the micellar aggregate described in the section B) to a lung, including nasally administering or intratracheally administering the pharmaceutical composition to an individual in need of intervention. Specifically, the pharmaceutical composition may be delivered to the lungs of an individual in need of intervention by being nasally or intratracheally administered to the individual in accordance with a conventional method using any appropriate administration instrument, such as a nebulizer, an endotracheal tube, or a microspray.

The individual in need of intervention is typically a human or a non-human mammal.

EXAMPLES

Now, the present invention is specifically described by way of Examples. However, the present invention is not limited to these Examples.

[Reagents, Cells, Experimental Animals Etc.]
  (1) Antisense oligonucleotides (ASOs) used were ASOs each having a phosphorothioate backbone (purchased from Gene Design Inc.).

The sequences of the ASOs are as follows (uppercase letters denote Locked Nucleic Acid (LNA) (C denotes LNA methylcytosine), and lowercase letters denote DNA).

ASO (asTUG1) targeting taurine upregulated gene 1 (TUG1) long non-coding RNA (lncRNA): 5'-TGAAt-ttcaatcatttgaGAT-3' (SEQ ID NO: 1)

GL3 luciferase-targeted ASO used as a control (asCTRL): 5'-TCGAagtactcagcgtaaGTT-3' (SEQ ID NO: 2)

A product obtained by attaching Alexa Fluor™ 647 dye to the 5'-end of asCTRL is represented as ASO-AF6. In addition, dibenzocyclooctyne (DBCO) was attached to the 3'-end of asTUG1, asCTRL, or ASO-AF6 for conjugation.

(2) A luciferase-expressing human lung cancer cell line, A549-Luc, was purchased from Caliper Lifesciences Corp. (Hopkinton, MA, USA) and was cultured in RPMI-1640 supplemented with 10% fetal bovine serum and 1% penicillin/streptomycin.

(3) A human pancreatic cancer cell line, Panc1, was purchased from American Type Culture Collection (Manassas, VA, USA) and was cultured in Dulbecco's modified Eagle's medium (DMEM) supplemented with 10% fetal bovine serum and 1% penicillin/streptomycin.

(4) BALB/c nude mice (female, 6 weeks old) were purchased from Charles River Japan (Kanagawa, Japan), and all animal experiments were performed under the Guidelines for the Care and Use of Laboratory Animals in The University of Tokyo.

Synthesis of Azide-terminated Poly(2-n-propyl-2-oxazoline)

Azide-terminated poly(2-n-propyl-2-oxazoline)s were synthesized by the following reaction scheme.

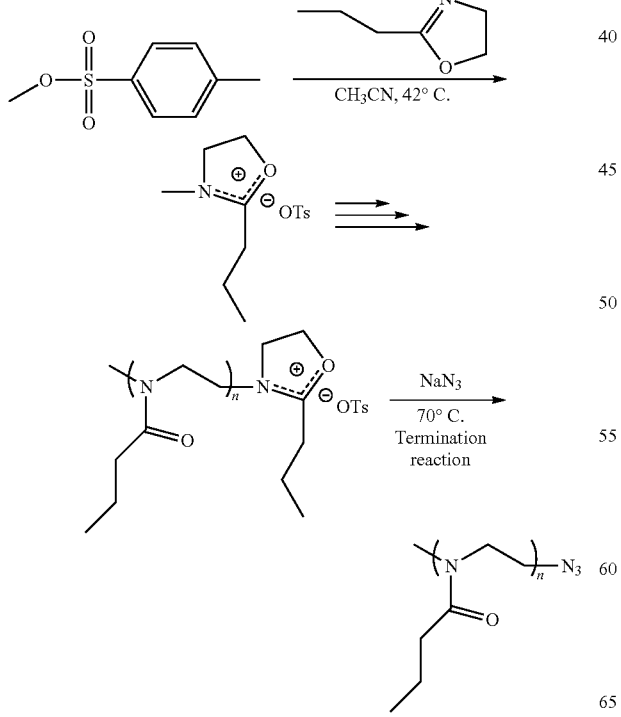

Specifically, the synthesis was performed as described below.

First, poly(2-n-propyl-2-oxazoline)s (PDXs) having four different molecular weights, that is, each having a molecular weight of about 5k, about 10k, about 20k, or about 30k were synthesized by living cationic ring-opening polymerization of 2-n-propyl-2-oxazoline.

For the synthesis of 5k or 10k PDX, methyl p-toluenesulfonate (61.6 mg, 0.332 mmol) serving as an initiator was dissolved in 5 mL or 10 mL of $CH_3CN$, followed by addition of 2-n-propyl-2-oxazoline (1.83 g, 16.2 mmol or 3.66 g, 32.4 mmol) respectively.

For the synthesis of 20k or 30k PDX, methyl p-toluenesulfonate (61.6 mg, 0.332 mmol) was dissolved in 20 mL or 30 mL of a 1:1 mixture solution of $CH_3CN$ and chlorobenzene (volume ratio), followed by addition of 2-n-propyl-2-oxazoline (7.32 g, 64.8 mmol or 11.0 g, 97.2 mmol), respectively.

The resultant mixture solutions were stirred for 4, 7, 12, or 16 days at 42° C. under an argon atmosphere to prepare PDX having a molecular weight of about 5k, about 10k, about 20k, or about 30k, respectively.

$NaN_3$ (432 mg, 6.64 mmol) was added to the mixture solutions and stirred at 70° C. for 3 hours to terminate the reaction. Then, the mixture solutions were dialyzed against methanol three times and deionized water three times, followed by lyophilization to recover the products as white powders.

The products were characterized by MALDI-TOF-MS (ultrafleXtreme; Bruker Daltonics, Bremen, Germany) using trans-2-[3-(4-tert-butylphenyl)-2-methyl-2-propenylidene] malononitrile as a matrix and using potassium trifluoroacetate as a cationized species. The obtained Mw and Mw/Mn are shown in Table 1.

TABLE 1

|  | $M_w$ | $M_n$ | $M_w/M_n$ |
| --- | --- | --- | --- |
| POX (5k) | 4,890 | 4,810 | 1.016 |
| POX (10k) | 10,100 | 10,030 | 1.007 |
| POX (20k) | 19,800 | 19,720 | 1.004 |
| POX (30k) | 30,200 | 30,080 | 1.004 |

[Preparation and Gel Electrophoresis of Conjugate between $N_3$-PDX and DBCO-ASO (PDX-ASO)]

A conjugate was obtained by allowing $N_3$-PDX and DBCO-ASO to react with each other through utilization of copper-free click chemistry with a freeze-thawing technique. The reaction scheme is shown below.

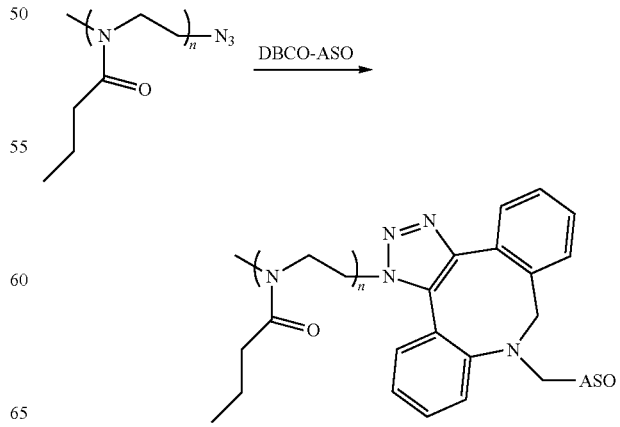

As a specific example of the preparation of PDX-ASO, a method of preparing PDX(30k)-ASO is described below.

N$_3$-PDX(30k) was dissolved in cooled 10 mM HEPES buffer (pH 7.3; VWR international, Radnor, PA, USA) at a concentration of 20 mg/mL, and then, mixed with asTUG1 solution (1 mg/mL in 10 mM HEPES) at varying molar ratios ([molar concentration of N$_3$ in PDX] to [molar concentration of DBCO in ASO]: (PDX/ASO)). The mixture solution was frozen at −20° C. overnight and was thawed at 4° C. for 2 hours. Thus, a conjugate between N$_3$-PDX(30k) and DBCO-ASO (PDX(30k)-ASO) was obtained.

[Gel Electrophoresis of PDX-ASO]

Agarose gel was prepared from agarose (1 wt %) dissolved in a TAE buffer (pH 7.4) containing 4 μg/mL ethidium bromide. Non-conjugated ASO and PDX(30k)-ASO samples were loaded on the gel and electrophoresed (100 V, 20 min) in the TAE buffer. The electrophoresed gel was visualized with a PharosFX molecular imager (Bio-Rad, Hercules, CA). Results are shown in FIG. 2.

Figure 2:
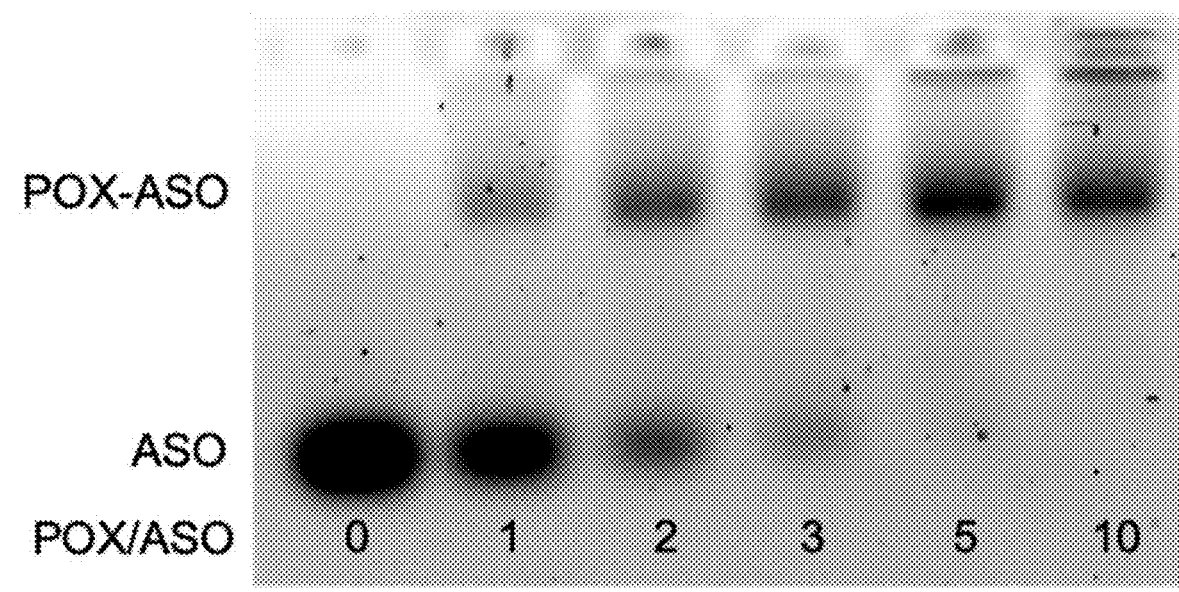
FIG. 2 is a gel photograph of agarose gel electrophoresis of PDX(30k)-ASO prepared at varied molar ratios of PDX to ASO (PDX/ASO). A conjugation rate at PDX/ASO=0, 1, 2, 3, 5, or 10 was 0%, 27.4%, 66.8%, 85.2%, 93.5%, or 98.8%, respectively.

As shown in FIG. 2, along with an increase in PDX/ASO, free ASO decreased, and conjugated PDX(30k)-ASO increased. In addition, the conjugation rates of DBCO-ASO were determined by quantifying the ASO-derived bands through use of ImageJ software. As a result, it was found that the amount of conjugated ASO (i.e., the amount of PDX-ASO) increased along with an increase in PDX/ASO, and almost all ASOs were conjugated with PDX(30k) at PDX/ASO=10 (conjugation rate: 98.8%).

[Purification and Size Exclusion Chromatography (SEC) of PDX-ASO]

Figure 3:
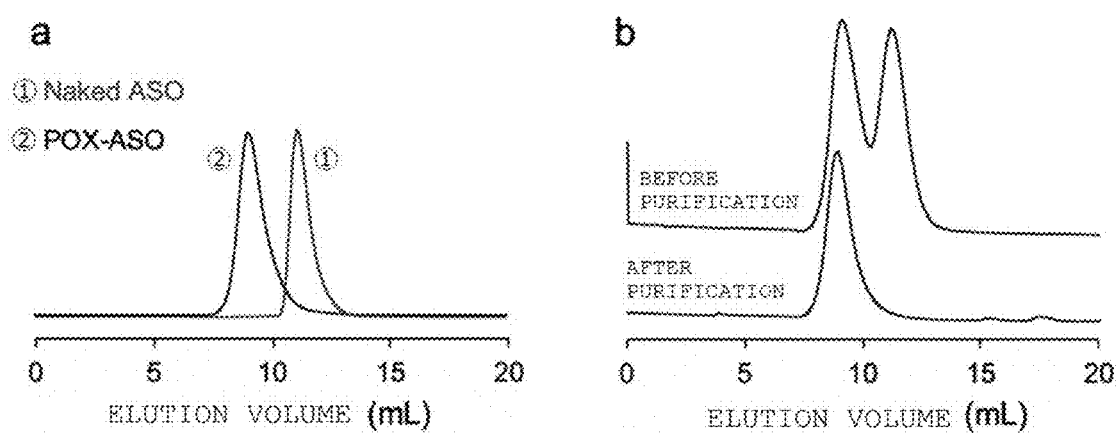
FIG. 3(a) includes SEC charts of naked ASO (DBCO-ASO) and PDX-ASO (PDX(30k)-ASO) before purification detected at a wavelength of 280 nm.
FIG. 3(b) includes SEC charts of PDX(30k)-ASO (PDX/ASO=10) before purification and after purification detected at a wavelength of 215 nm.

The PDX(30k)-ASO sample prepared at PDX/ASO=10 was lyophilized, dispersed in acetone to remove excess PDX, and then, centrifuged to obtain PDX-ASO as a precipitate. The supernatant including unreacted PDX was decanted, the precipitate was dispersed in acetone again, and the same process was repeated four times. Then, the precipitate was dissolved in deionized water and lyophilized. The final product was subjected to SEC using an AKTA explorer100 system equipped with a Superdex 75 10/300 GL column (GE Healthcare Life Sciences, Pittsburgh, PA, USA) using 10 mM HEPES buffer (pH 7.3) containing 150 mM NaCl at 4° C. ASO was detected by UV at a wavelength of 280 nm before and after conjugation. Results are shown in FIG. 3a. In addition, PDX was detected by UV at a wavelength of 215 nm before and after purification. Results are shown in FIG. 3b.

As shown in FIG. 3a, the PDX(30k)-ASO sample prepared at PDX/ASO=10 showed a unimodal peak shifted from the peak of DBCO-ASO for absorption at a wavelength of 280 nm. In addition, as shown in FIG. 3b, the PDX(30k)-ASO sample after purification showed a clear unimodal peak for absorption at a wavelength of 215 nm. These results indicate that the click conjugation of N$_3$-PDX(30k) and DBCO-ASO and the purification of PDX(30k)-ASO proceeded as intended.

[Preparation of Micellar Aggregates (ASOballs) of PDX-ASO]

The purified PDX-ASO conjugates were dissolved in 10 mM HEPES buffer containing 150 mM NaCl at 4° C., followed by dilution with the same buffer to designated concentrations (10 μM ASO for in vitro studies and 40 μM ASO for in vivo studies). After incubation at 4° C. for 20 minutes, the sample solutions were additionally incubated at 37° C. for 20 minutes for preparation of ASOballs.

[Light Scattering Analysis of ASOballs]

Figure 4:
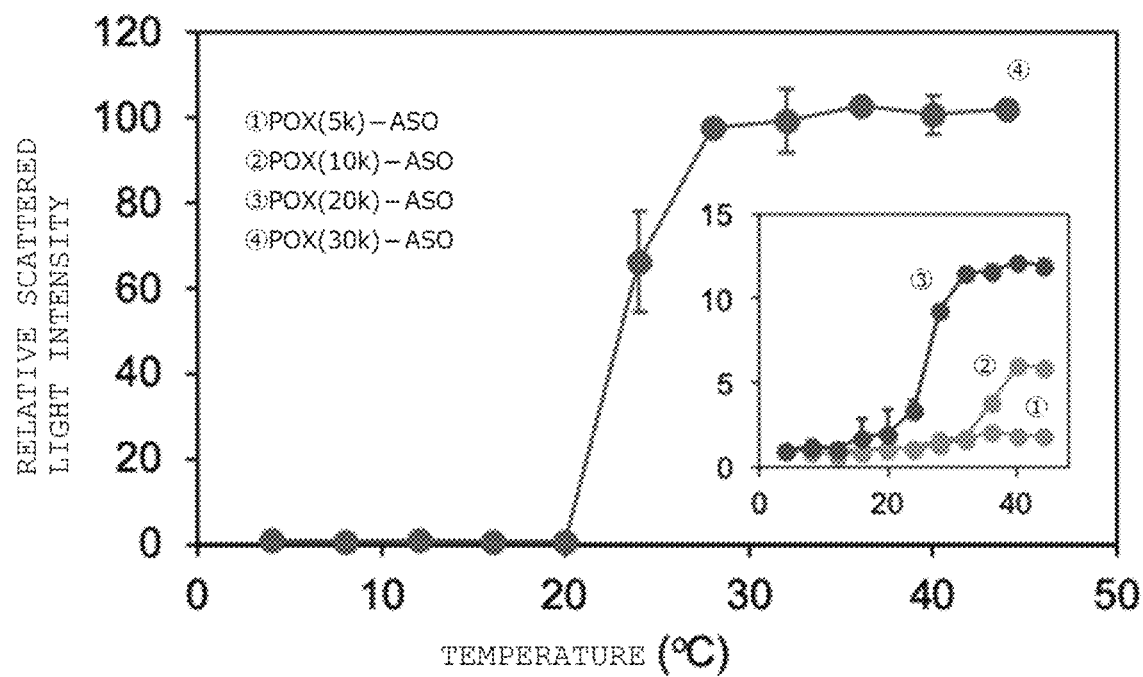
FIG. 4 is a graph showing relative scattered light intensities determined by static light scattering measurement performed at an ASO concentration of 10 μM and various temperatures. Results are expressed as mean±standard deviation (n=3).
Figure 5:
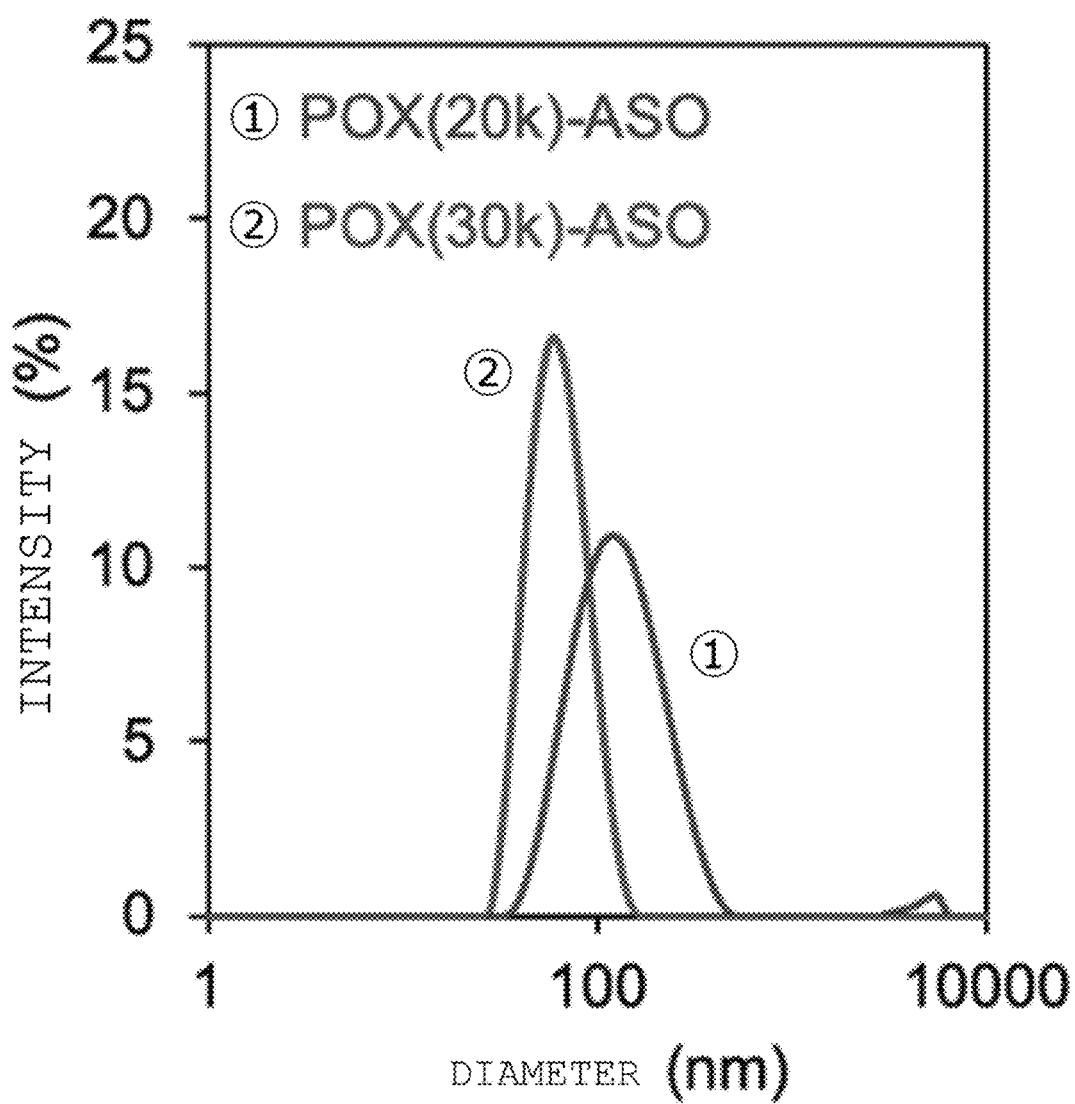
FIG. 5 includes size distribution histograms of ASOballs, determined by DLS measurement at 37° C. and an ASO concentration of 10 μM.

Various PDX-ASO solutions containing 10 μM asTUG1 were added to a low-volume quartz cuvette (Malvern Instruments, Worcestershire, UK) and a scattered light intensity was obtained by static light scattering measurement using a Zetasizer Nano-ZS instrument (Malvern Instruments) with increased temperatures. The temperature was increased at 1° C./min to the next designated temperature and equilibrated for 2 minutes. The scattered light intensity was sequentially measured and normalized to the initial value of each sample (i.e., scattered light intensity at 4° C.). Results are shown in FIG. 4. In addition, at 37° C., the hydrodynamic diameter ($D_H$) and polydispersity index (PDI) of ASOballs were determined by dynamic light scattering (DLS) measurement and their zeta-potential was determined by electrophoretic light scattering (ELS). Results are shown in Table 2. In addition, DLS histograms are shown in FIG. 5.

TABLE 2

| ASOballs | $D_H$ (nm) [a] | PDI[a] | Zeta-potential (mV) [b] |
|---|---|---|---|
| POX (5k)-ASO | 418 ± 48 | 0.39 ± 0.11 | −28 ± 3 |
| POX (10k)-ASO | 148 ± 52 | 0.53 ± 0.18 | −28 ± 4 |
| POX (20k)-ASO | 116 ± 20 | 0.17 ± 0.09 | −22 ± 4 |
| POX (30k)-ASO | 49 ± 3 | 0.08 ± 0.05 | −21 ± 3 |

[a] measured by DLS at 37° C. (mean ± s.d., n = 4).
[b] measured by ELS at 37° C. (mean ± s.d., n = 4).

As shown in FIG. 4, in all PDX-ASO sample solutions, an increase in relative scattered light intensity value was observed in the temperature range of from about 20° C. to about 40° C. This indicates that those PDX-ASOs each had an LCST within the temperature range of from about 20° C. to about 40° C., and formed aggregates (ASOballs) derived from the transition of the PDX segment from hydrophilic to hydrophobic at the LCST (LCST of each PDX-ASO: 5k=about 30° C., 10k=about 30° C., 20k=about 22° C., 30k=about 20° C.). In addition, the increase in relative scattered light intensity value with the increase in temperature was remarkable in the PDX-ASO with a longer PDX segment. Additionally, the temperature at which the relative scattered light intensity value began to increase gradually decreased as the molecular weight of the PDX segment increased. These results suggest that the molecular weight of the PDX segment affects the self-assembling behavior of the PDX-ASO, presumably due to the varying hydrophobic aggregation force of each PDX segment depending on the molecular weight.

In addition, as shown in Table 2, the ASOballs formed from PDX(5k)-ASO and PDX(10k)-ASO having relatively short PDX segments showed polydispersity indices of more than 0.3, whereas the ASOballs formed from PDX(20k)-ASO and PDX(30k)-ASO showed low polydispersity indices of less than 0.2, as demonstrated from unimodal peaks in FIG. 5, indicating the formation of homogeneous aggregates. Especially, the ASOballs formed from PDX(30k)-ASO exhibited a remarkably low polydispersity index of 0.08. In addition, the fact that ASOballs show a negative zeta-potential indicates the formation of micellar aggregates each having a core formed by a hydrophobic PDX segment and a negatively charged ASO shell. Nanoparticles larger than 100 nm may be subjected to the phagocytic clearance of alveolar macrophages, and hence the following experiments were performed using ~50 nm-sized ASOballs formed from PDX(30k)-ASO.

[Transmission Electron Microscopy (TEM) Observation]

The ASOballs prepared from the PDX(30k)-ASO were subjected to TEM observation as described below.

A droplet of a PDX(30k)-ASO sample at a concentration of 10 µM asTUG1 dissolved in deionized water at 37° C. or 4° C. was placed on a mesh copper grid with a carbon-coated collodion and stained with 2 wt % uranyl acetate in 50% methanol. TEM images were obtained with a JEM-1400 (JEOL Ltd., Tokyo, Japan) at 120 kV (FIG. 6a and FIG. 6b).

Figure 6:
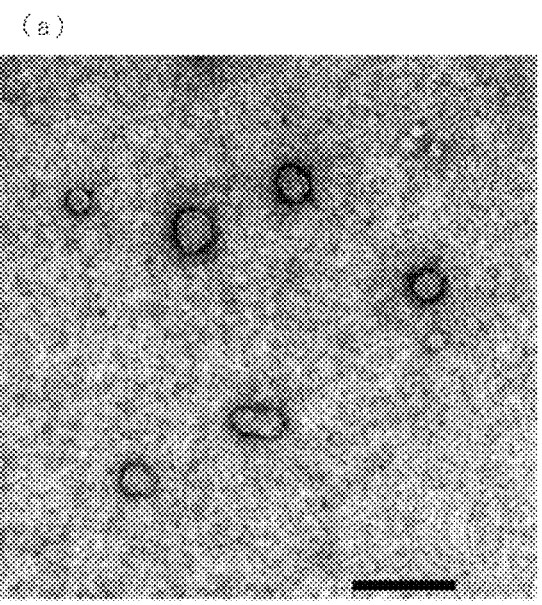
FIG. 6(a) is a TEM image of PDX(30k)-ASOballs prepared at 37° C. and an ASO concentration of 1 μM.
FIG. 6(b) is a TEM image of PDX(30k)-ASO prepared at 4° C. and an ASO concentration of 1 μM. In each of FIG. 6(a) and FIG. 6(b), the scale bar represents 100 nm.
Figure 6:

As shown in FIG. 6a, in the PDX(30k)-ASO sample incubated at 37° C., ~50 nm-sized spherical structures were observed clearly. In contrast, no distinguishable structures were observed in the PDX(30k)-ASO sample incubated at 4° C. (FIG. 6b). Those observation results are consistent with the results obtained from the light scattering analysis.

[Fluorescence Correlation Spectroscopy (FCS) Analysis]

The critical micelle concentration (CMC) of ASOballs and the association number of PDX-ASO per ASOball were determined by FCS analysis.

The FCS analysis was performed using Zeiss LSM 880 equipped with a ConfoCor3 module and a C-Apochromat 40× water objective lens (Carl Zeiss, Oberkochen, Germany).

Figure 7:
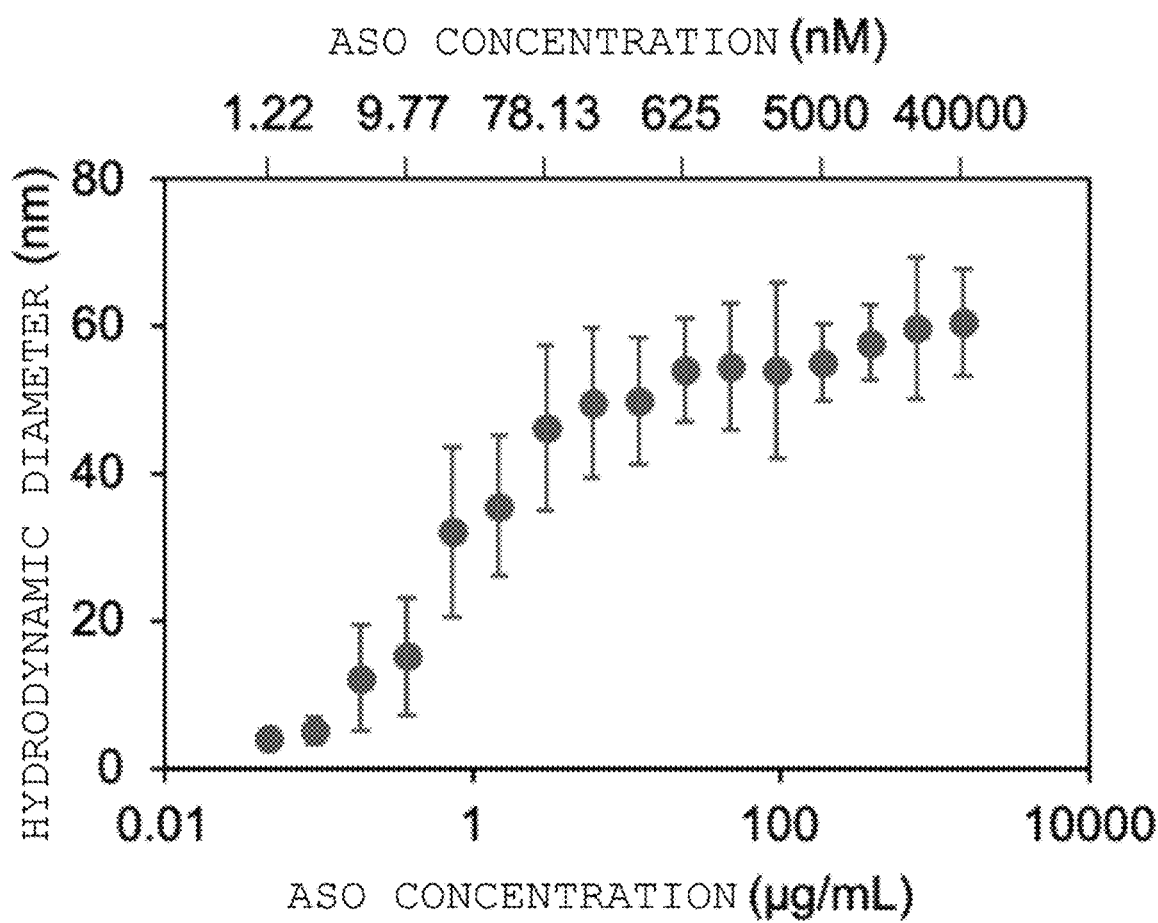
FIG. 7 is a graph showing concentration-dependent changes in hydrodynamic diameter of PDX(30k)-ASO, determined by FCS analysis. Results are expressed as mean±standard deviation (sampling time: 10 seconds and number of repetitions: 20).

For the CMC of ASOballs, a PDX(30k)-ASO-AF6 solution obtained by dissolving the PDX(30k)-ASO-AF6 at an ASO concentration of 40 µM in 10 mM HEPES buffer containing 150 mM NaCl was left at rest at 37° C. to prepare an ASOball sample. Serially diluted samples at various concentrations were placed into an 8-well Lab-Tek chamber (Nalge Nunc International, Rochester, NY, USA) and fluorescence detection was carried out using a 561 nm DPSS laser for excitation and a 588-691 nm band pass filter for emission. Diffusion times were obtained by a sampling time of 10 seconds and a number of repetitions of 20. Diffusion coefficients ($D_C$) were calculated from the obtained diffusion times based on a reference of Cy5 maleimide (GE Healthcare, UK). Hydrodynamic diameters ($D_H$) were calculated from $D_C$ based on the Strokes-Einstein equation: $D_H=k_BT/3\pi\eta D_C$ ($k_B$: Boltzmann's constant, T: absolute temperature, η: dynamic viscosity). Results are shown in FIG. 7.

A fluorescence intensity per non-conjugated ASO molecule or per ASOball (CPM) was respectively determined by FCS analysis for a non-conjugated ASO-AF6 sample or an ASOball sample prepared from a mixture of 90% PDX(30k)-ASO and 10% PDX(30k)-ASO-AF6. The association number of PDX-ASO per ASOball ($AN_{POX-ASO}$) was calculated using the following equation with the obtained CPMs: $AN_{POX-ASO}=CPM_{ASOball}/CPM_{ASO}\times 10$. Results are shown in Table 3.

TABLE 3

| ASO conc. (nM) | CPM (kHz) ASO-AF6 | ASOballs (10% POX-ASO-AF6, 90% POX-ASO) | CPM ratio (ASOballs/ ASO-AF6) | $AN_{POX-ASO}$ |
|---|---|---|---|---|
| 312.5 | 3.1 ± 0.3 | 93.5 ± 25.5 | 30 | 300 |
| 625 | 1.9 ± 0.2 | 58.3 ± 15.2 | 31 | 310 |
| 1,250 | 1.1 ± 0.2 | 32.2 ± 4.3 | 29 | 290 |
| 2,500 | 0.5 ± 0.2 | 15.3 ± 2.7 | 31 | 310 |

As shown in FIG. 7, the ASOballs maintained hydrodynamic diameters of from 30 nm to 60 nm at ASO concentrations of from about 10 nM or more to at least 40 µM (i.e., PDX(30k)-ASO concentrations of about 10 nM (about 0.8 µg/mL) or more). In contrast, the size of the ASOballs exhibited a considerable decrease at ASO concentrations of less than 10 nM and eventually reached a size of about 5 nm at an ASO concentration of about 1 nM. The size of 5 nm may correspond to the free PDX-ASO. In general, a pharmaceutical composition for intratracheal administration is often concentrated from the viewpoint of a higher dose, and this concentration process likely induces secondary aggregation. However, it is found from the above-mentioned results that the ASOballs do not undergo secondary aggregation even at a concentration of 40 µM, and hence are excellent in stability. Of note, in the FCS analysis performed for the size measurement, a higher signal/noise ratio was provided, compared to DLS, under highly dilute conditions.

In addition, as shown in Table 3, the CPMs obtained from ASOball samples were about 30-fold higher than those of non-conjugated ASO-AF6 regardless of the ASO concentrations, indicating that the number of PDX-ASOs contained in a single ASOball was approximately 300. When ASOballs prepared from PDX(20k)-ASO were subjected to similar analysis, $AN_{POX-ASO}$ was about 700 at ASO concentrations of 1.25 µM and 2.5 µM. The association number was larger than that of the ASOballs prepared from PDX(30k)-ASO, and this result is apparently consistent with their relationship in DLS histograms.

[In Vitro Gene Knockdown Assay]

The gene knockdown efficiency of ASOballs was investigated using A549-Luc cells serving as cultured human lung carcinoma cells. Here, asTUG1 was used as the ASO. TUG1 lncRNA, which is targeted by asTUG1, is frequently overexpressed in various types of cancers including lung carcinoma, and known to regulate the proliferation and apoptosis of A549 cells.

ASOball samples were prepared at an asTUG1 (or asCTRL) concentration of 10 µM in 10 mM HEPES buffer containing 150 mM NaCl at 37° C. Cultured A549-Luc cells were transfected with non-conjugated ASO or ASOballs at ASO concentrations of 100 nM and 200 nM. After 48 hours of incubation, the cells were rinsed with PBS and RNA was extracted using RNeasy Mini Kit (Qiagen, Valencia, CA, USA). Genomic DNA was eliminated, cDNA was synthesized using ReverTra Ace (Toyobo, Osaka, Japan), and qRT-PCR was performed using FastStart Universal SYBR-Green Master (Roche, Basel, Switzerland) and ABI 7500 Fast Real-time PCR System (Applied Biosystems, Foster City, CA, USA). An endogenous house-keeping gene, GAPDH, was employed to determine a relative expression level of TUG1 lncRNA. Results are expressed as mean and standard deviation in FIG. 8 (n=4, *p<0.001 and **p<0.0001).

Further, the knockdown efficiency of asTUG1balls against Panc1 cells was determined by qRT-PCR. The ASO transfection of this cell line, mRNA purification, and reverse transcription were performed as described for the A549-Luc cells. Results are expressed as mean and standard deviation in FIG. 9 (n=4, *p<0.05).

Primer sequences used in qRT-PCR are as follows.

<Primer Sequence for GAPDH>
   forward 5'-CCA CCC ATG GCA AAT TCC-3' (SEQ ID NO: 3)
   reverse 5'-CAG GAG GCA TTG CTG ATG AT-3' (SEQ ID NO: 4)

<Primer Sequence for TUG1>
   forward 5'-AGG TAG AAC CTC TAT GCA TTT TGT G-3' (SEQ ID NO: 5)
   reverse 5'-ACT CTT GCT TCA CTA CTT CAT CCA G-3' (SEQ ID NO: 6)

Figure 8:
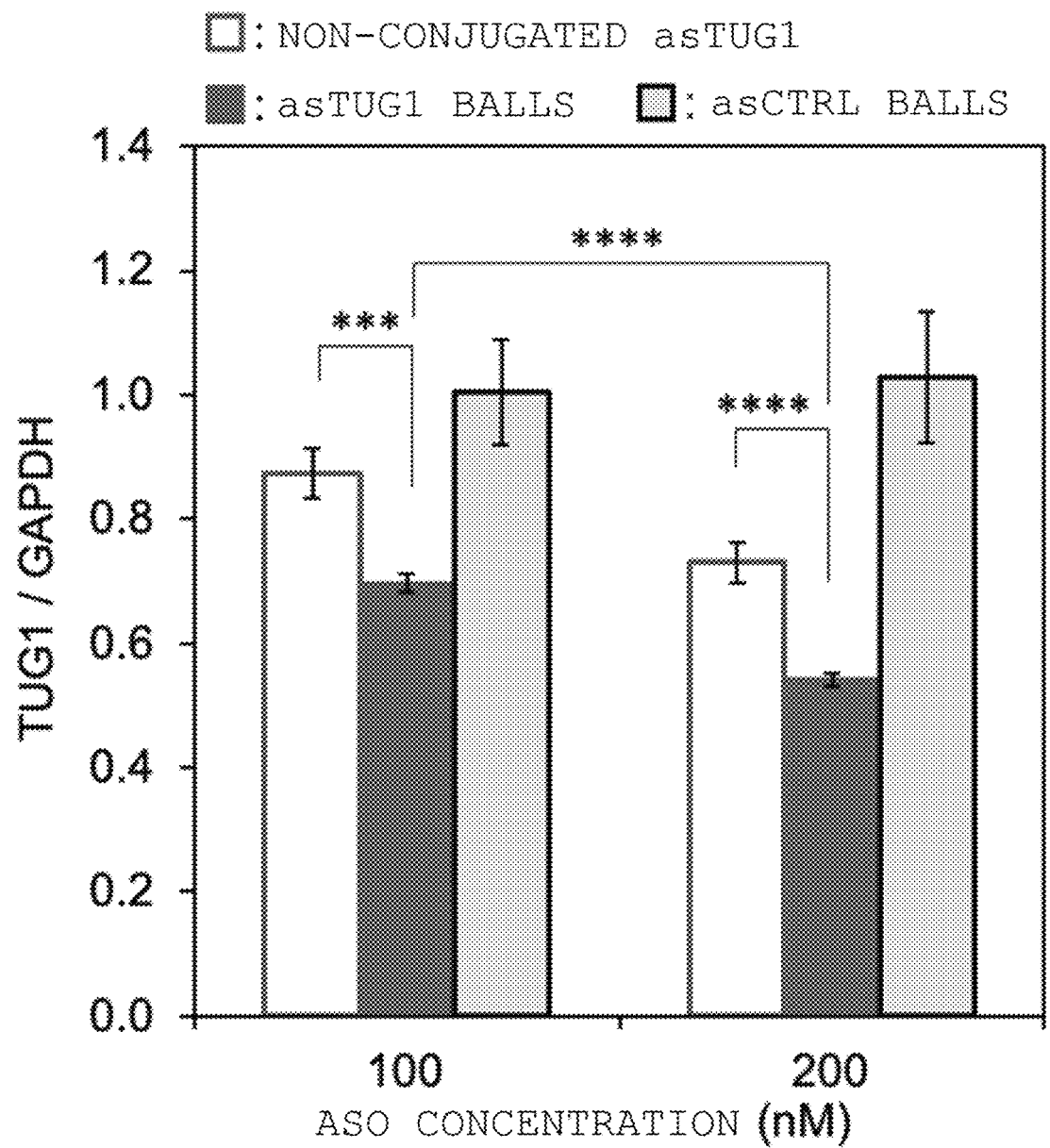
FIG. 8 is a graph showing TUG1 lncRNA expression levels hours post-transfection with non-conjugated asTUG1 or asTUG1balls, determined by qRT-PCR assay, for A549-Luc cells. Results are expressed as mean±standard deviation (n=4; *$p<0.001$ and **$p<0.0001$).

As shown in FIG. 8, non-conjugated TUG1-targeted ASO (asTUG1) induced modest gene knockdown in a concentration-dependent manner. The gene knockdown ability of asTUG1 is presumably due to the PS backbone and LNA wings, which enhance the tolerability against nucleases and the binding affinity to target RNA. In contrast, asTUG1-loaded ASOballs (asTUG1balls) elicited the significantly greater knockdown of TUG1 lncRNA as compared to non-conjugated asTUG1. Meanwhile, no decrease in TUG1 expression level was observed in the cells treated with asCTRL-loaded ASOballs (asCTRLballs). These results demonstrate that ASOballs have a sequence-specific gene knockdown ability.

Figure 9:
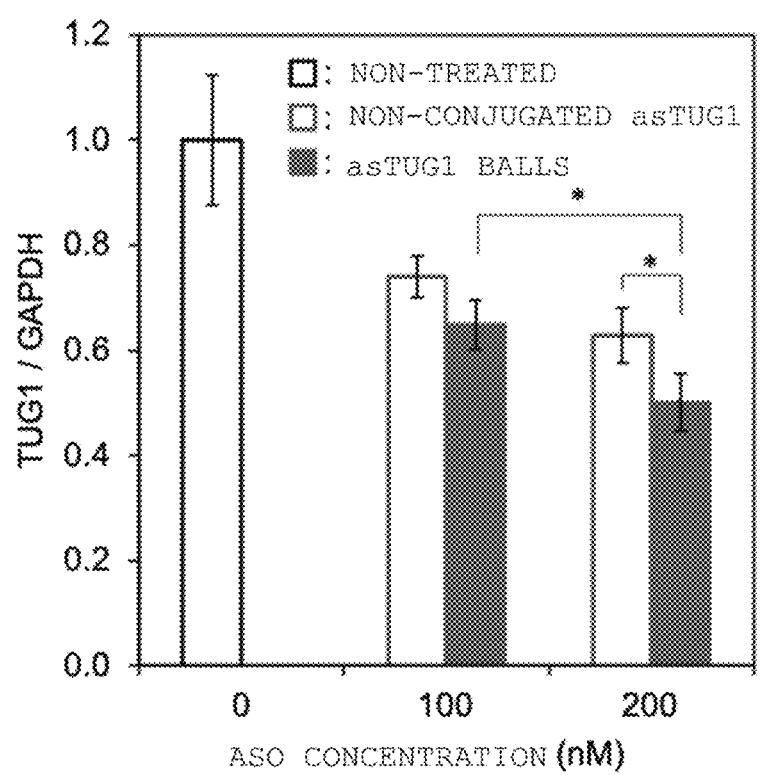
FIG. 9 is a graph showing TUG1 lncRNA expression levels hours post-transfection with non-conjugated asTUG1 or asTUG1balls, determined by qRT-PCR assay, for Panc1 cells. Results are expressed as mean±standard deviation (n=4; *$p<0.05$).

In addition, as shown in FIG. 9, when the gene knockdown ability of ASOballs was evaluated for human pancreatic cancer Panc1, which overexpresses TUG1 lncRNA, the ASOballs elicited a significant reduction in the expression level of TUG1 lncRNA in cultured Panc1 cells. This indicates that the gene knockdown ability of ASOballs is not limited for the specific cell lines.

Considering that the PDX-ASO used in the gene knockdown assay does not contain a specific cleavable linker between the PDX segment and the ASO, the significant gene knockdown activity of ASOballs indicates that the ASOballs and/or dissociated PDX-ASO should be efficiently bound to the target lncRNA. The sizes of 21mer ASO and PDX(30) in a hydrophobic state are estimated to be about 3.5 nm and about 2.5 nm, respectively. When the ASOballs were dissociated inside the target cells through lowering of their concentration, the ~2.5 nm-sized PDX conjugated at the 3'-end of ASO may not substantially hinder the hybridization between ASO and target lncRNA.

[Cellular Uptake Evaluation]

Cellular uptake evaluation using ASO-AF6 was performed in cultured A549-Luc cells.

ASOball samples were prepared at an ASO-AF6 concentration of 10 µM in 10 mM HEPES buffer containing 150 mM NaCl at 37° C. Cultured A549-Luc cells were transfected with non-conjugated ASOs or ASOballs at ASO concentrations of 100 nM and 200 nM. After 6 hours of culture, the cells were rinsed with PBS twice and fresh PBS was added to the cells. The fluorescence intensity of ASO-AF6 was measured using a microplate reader (Tecan Spark™ Mannedorf Switzerland) and a relative fluorescence intensity was calculated from the obtained fluorescence value as a percentage of non-treated control wells. Results are expressed as mean and standard deviation in FIG. 10 (n=4, p<0.01 and **p<0.0001).

Figure 10:
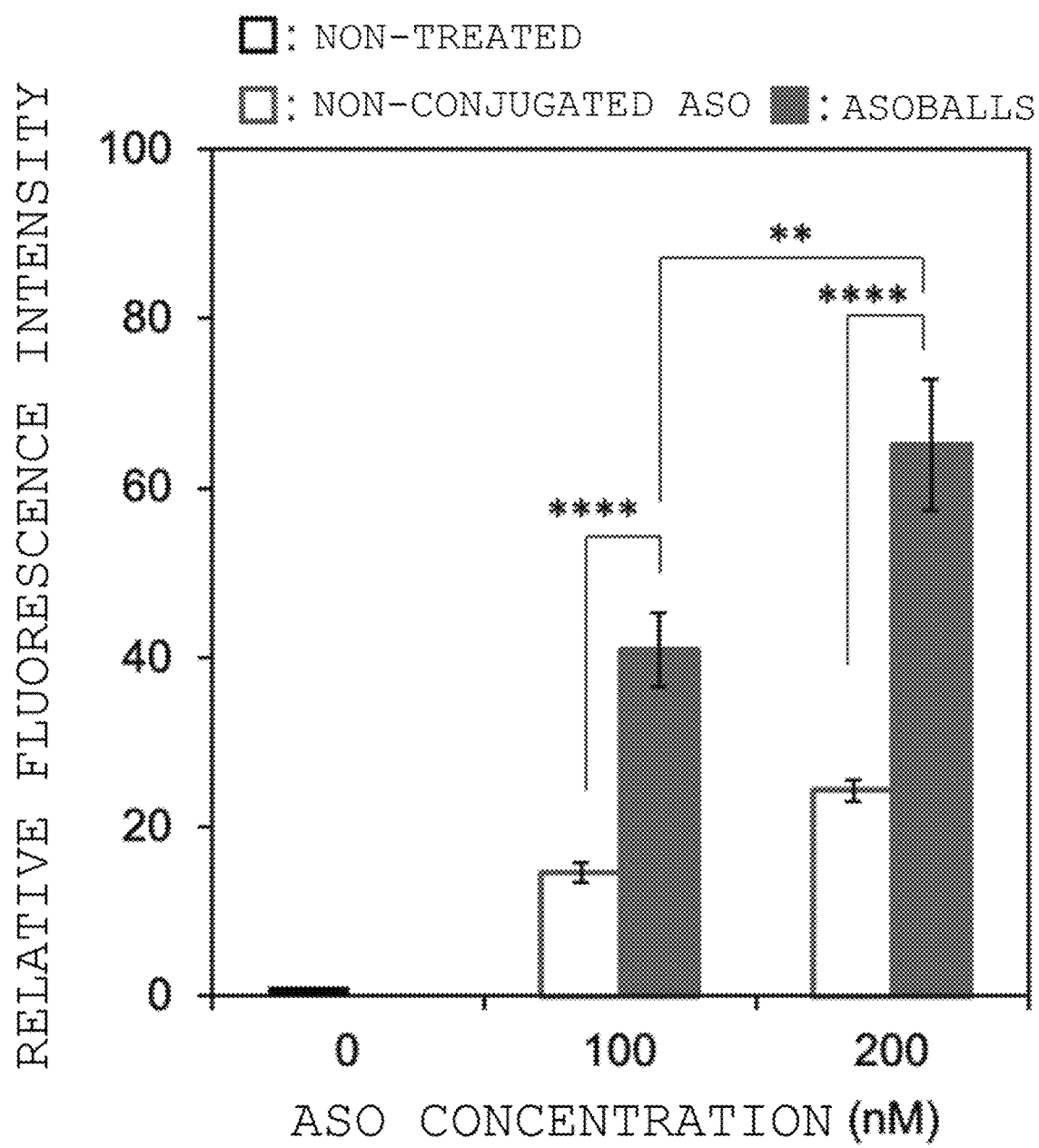
FIG. 10 is a graph showing cellular uptake efficiency 6 hours post-transfection with non-conjugated ASO-AF6 or ASO-AF6balls, determined from fluorescence intensity, for A549-Luc cells. Results are expressed as mean±standard deviation (n=4; $p<0.01$ and **$p<0.0001$).

As shown in FIG. 10, the ASOballs showed significantly enhanced cellular uptake efficiency as compared to the non-conjugated ASO. This result is consistent with the higher gene knockdown activity of the ASOballs than that of the non-conjugated ASO.

[Cell Viability Assay]

ASOball samples were prepared at an asCTRL concentration of 10 µM in 10 mM HEPES buffer containing 150 mM NaCl at 37° C. Cultured A549-Luc cells were transfected with non-conjugated ASOs or ASOballs at ASO concentrations of 100 nM, 200 nM, 400 nM, 800 nM, and 1,600 nM. After 48 hours of culture, the medium was exchanged and cell viability was evaluated with Cell Counting Kit-8 (Dojindo, Kumamoto, Japan). Absorption at 450 nm was measured using Tecan Spark™ and a relative absorbance was calculated from the obtained absorption value as a percentage of non-treated control wells. Results are expressed as mean and standard deviation in FIG. 11 (n=4).

Figure 11:
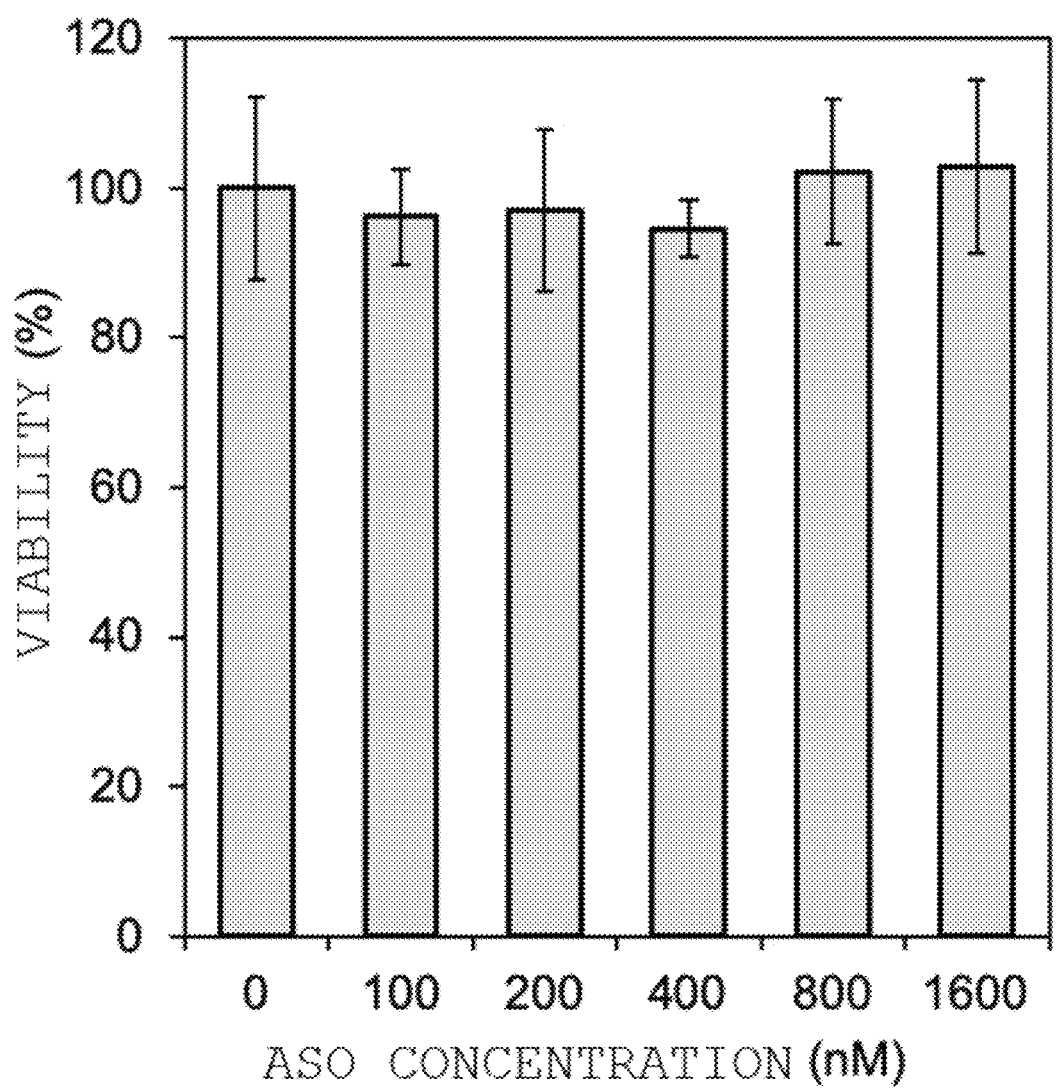
FIG. 11 is a graph showing cell viability 48 hours post-transfection with asCTRLballs, for A549-Luc cells. Results are expressed as mean±standard deviation (n=4).

As shown in FIG. 11, the ASOballs elicited negligible cytotoxicity up to an ASO concentration of 1.6 µM.

[Biodistribution of ASOballs in Orthotopic Xenograft Tumor Model]

In order to investigate ASO delivery by ASOballs through intratracheal administration, a biodistribution in an orthotopic lung cancer model mouse was investigated.

1. Generation of Orthotopic Xenograft Tumor Model

BALB/c nude mice (female, 6 weeks old) were anesthetized with isoflurane and tumor implantation was performed according to a method of the published studies with some modification. That is, a 5 mm incision was made in the dorsal skin over the left lung of the mice, and then, $3 \times 10^6$ A549-Luc cells suspended in 40 µL PBS/Matrigel (1:1, v/v) were inoculated directly into the lung parenchyma at a depth of 3 mm using a needle of 30 G (326668; BD, Franklin Lakes, NJ, USA). The wound was closed with surgery clips and the mice were placed on a heating pad until they awoke from anesthesia. Establishment of lung cancer and the cancer growth were monitored by In Vivo Imaging System (IVIS; PerkinElmer, Waltham, MA, USA) and bioluminescent images were obtained 10 minutes after D-luciferin intraperitoneal injection. When the bioluminescence signal intensity of tumors reached $10^7$ to $10^8$ photons/s per tumor, intratracheal administration was carried out.

2. Intratracheal Administration

Under anesthesia using isoflurane, the trachea of the A549-Luc tumor-bearing mice was surgically exposed, and a small incision was made on the trachea. A sample were injected into the trachea using MicroSprayer™ Aerosolizer (MSA-250-M; Penn-Century, Inc., Wyndmoor, PA, USA). The incision was closed with sutures and the mice were placed on a heating pad until they awoke from anesthesia. In order to prevent the ASOballs from being dissociated into single PDX-ASO during the administration process, the ASO concentration in a sample solution was adjusted to 40 µM (the concentration being a concentration sufficiently higher than the CMC of the ASOballs). In addition, the temperature of the sample solution or MicroSprayer™ Aerosolizer was maintained at 37° C. until immediately before the administration through use of a heat plate, and the sample solution was quickly administered within 3 minutes. The ASOballs have been recognized to be stable at 25° C. for at least 15 minutes, and hence, according to the administration method described above, the micellar structure of the ASOballs can be maintained during the administration process.

3. Biodistribution Evaluation

Figure 12:
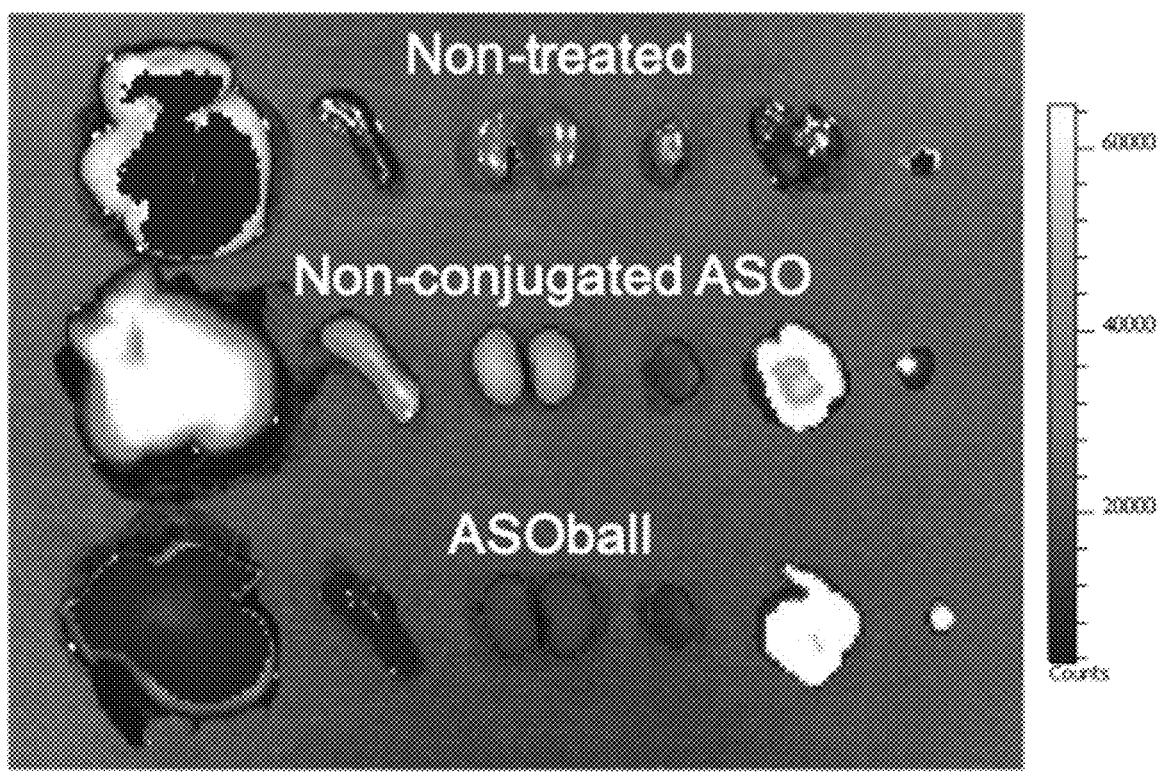
FIG. 12 is an ex vivo image of excised organs and tissues by IVIS.

ASOball samples were prepared at an ASO-AF6 concentration of 40 µM in 10 mM HEPES buffer containing 150 mM NaCl at 37° C. Intratracheal administration of non-conjugated ASO-AF6s and ASOballs (50 µL, about 17 µg ASO/mouse, n=4) into the orthotopic xenograft mice was carried out as described above. At 24 hours post-administration, the mice were sacrificed, and individual organs including liver, spleen, kidney, heart, and lung were excised. Tumors were separated from the lungs of the mice. The fluorescent signals of ASO-AF6 in tissues were observed with IVIS (FIG. 12). Then, each tissue was weighed and homogenized, and the fluorescence intensity was detected with Tecan Spark™. Results are expressed as mean and standard deviation in FIG. 13 (n=4, p<0.01 and **p<0.0001).

Figure 13:
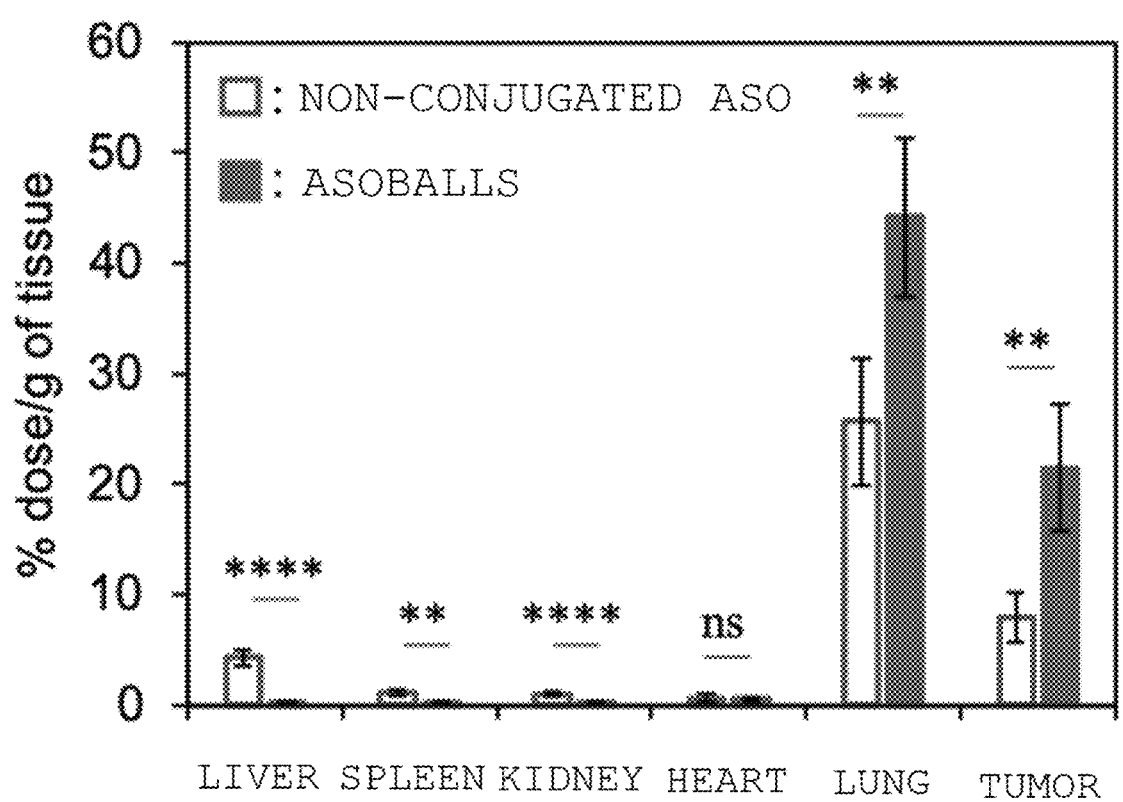
FIG. 13 is a graph showing the fluorescence intensities of homogenized organs (liver, spleen, kidney, heart, and lung) and tumors measured by a microplate reader 24 hours post-administration. Results are expressed as mean±standard deviation (n=4; $p<0.01$ and **$p<0.0001$).

As shown in FIG. 13, while both non-conjugated ASOs and ASOballs displayed considerably high fluorescence intensities in the lung and the tumor, the fluorescence intensities of the ASOballs (44±7% and 26±6% dose $g^{-1}$ tissue in the lung and the tumor, respectively) were significantly higher than the fluorescence emissions of the non-conjugated ASOs (22±6% and 8±2% dose $g^{-1}$ tissue in the lung and the tumor, respectively).

In addition, the non-conjugated ASOs were observed to accumulate in the liver, the spleen, and the kidney (4.3±0.7%, 1.2±0.3%, and 1.0±0.2% dose $g^{-1}$ tissue in the liver, the spleen, and the kidney, respectively), whereas the ASOballs exhibited almost undetectable accumulation in these organs (<0.3% dose $g^{-1}$ tissue). These results indicate that a considerable amount of the non-conjugated ASOs escaped from the lung to the systemic circulation and subsequently accumulated in the other organs. In contrast, it is presumed that the ASOballs suppressed the clearance to the systemic circulation, due to the larger size of 50 nm, resulting in significant increases in ASO accumulation amounts in the lung and the lung tumor.

[In Vivo Gene Knockdown Assay]

The in vivo knockdown of TUG1 lncRNA by ASOballs in the orthotopic lung tumor was determined by qRT-PCR assay.

ASOball samples were prepared at an asTUG1 or asCTRL concentration of 40 µM in 10 mM HEPES buffer containing 150 mM NaCl at 37° C. Intratracheal administration of non-conjugated asTUG1 and ASOballs (50 µL, ~15 µg ASO/mouse, n=4) into the orthotopic xenograft mice was carried out in the same manner as described above. At 72 hours post-administration, the mice were sacrificed and the lungs were excised. Tumors were separated from the lungs of the mice and homogenized. RNA was extracted using an RNeasy Mini kit and the relative expression amounts of TUG1 lncRNA with respect to GAPDH mRNA were quantified by qRT-PCR in the same manner as described above. Results are expressed as mean and standard deviation in FIG. 14 (n=4, **p<0.01). Of note, the asTUG1 used in this experiment was designed to target human TUG1 lncRNA, and thus the obtained results reflect the gene knockdown effect only in the human-derived cancer cells, not showing the gene knockdown effect in the host murine cells.

Figure 14:
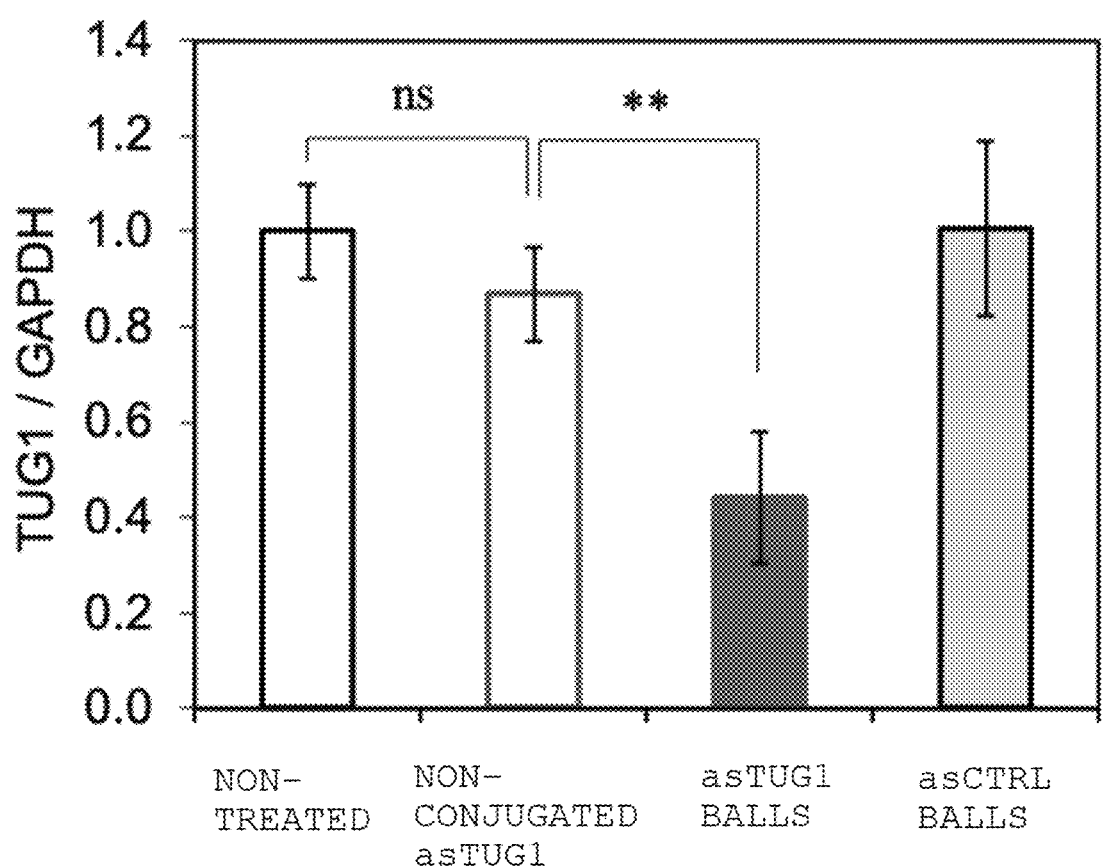
FIG. 14 is a graph showing TUG1 lncRNA expression levels in tumors 72 hours post-administration, determined by qRT-PCR assay. Results are expressed as mean±standard deviation (n=4; **$p<0.01$).

As shown in FIG. 14, at 72 hours post-administration, the intratracheally administered asTUG1balls (15 µg ASO/mouse) significantly reduced the expression level of TUG1 lncRNA by ~55% in the tumor, whereas no reduction in TUG1 lncRNA expression level was observed in the asCTRLball administration group. These results demonstrate that the intratracheally administered ASOballs exhibit a sequence-specific gene knockdown ability in the lung tumor.

Meanwhile, non-conjugated asTUG1 did not elicit a significant gene knockdown effect in the tumor. Such difference in gene knockdown ability may be due to the enhanced cellular uptake efficiency or facilitated intracellular processes of the ASOballs as compared to the non-conjugated ASOs, although the cause is not identified.

Notably, the ASOballs exhibited 55% gene knockdown at the dose of 15 µg ASO/mouse, while, according to a previous report, a dose of 40 µg ASO/mouse or 100 µg ASO/mouse was required for performing 50% or 65% gene knockdown with ASO alone (naked ASO), respectively (Plos One, 2017, 12, e0187286). Thus, the formation and intratracheal administration of the ASOballs can be expected to reduce the dose of ASO for the gene knockdown in the lung or lung tumor.

[Adjustment of Size of ASOballs by Addition of PDX]

The PDX(30k)-ASO conjugates were dissolved in 10 mM HEPES buffer containing 150 mM NaCl at 4° C., followed by dilution with the same buffer to 10 µM ASO. The resultant PDX(30k)-ASO solution was mixed with an equal volume of a PDX(30k) solution prepared at 10 µM with the same buffer, and the mixture was left at rest at 4° C. for 20 minutes. After that, the mixture was further left at rest at 37° C. for 20 minutes to prepare ASOballs.

The above-mentioned ASOball solution and an ASOball solution prepared in the same manner except for mixing with 10 mM HEPES buffer containing 150 mM NaCl in place of the PDX(30k) solution (as a result, PDX(30k) was not added) were added to a low-volume quartz cuvette (Malvern Instruments, Worcestershire, UK) and DLS analysis was performed at 37° C. using a Zetasizer Nano-ZS instrument (Malvern Instruments). The obtained DLS histograms are shown in FIG. 15.

Figure 15:
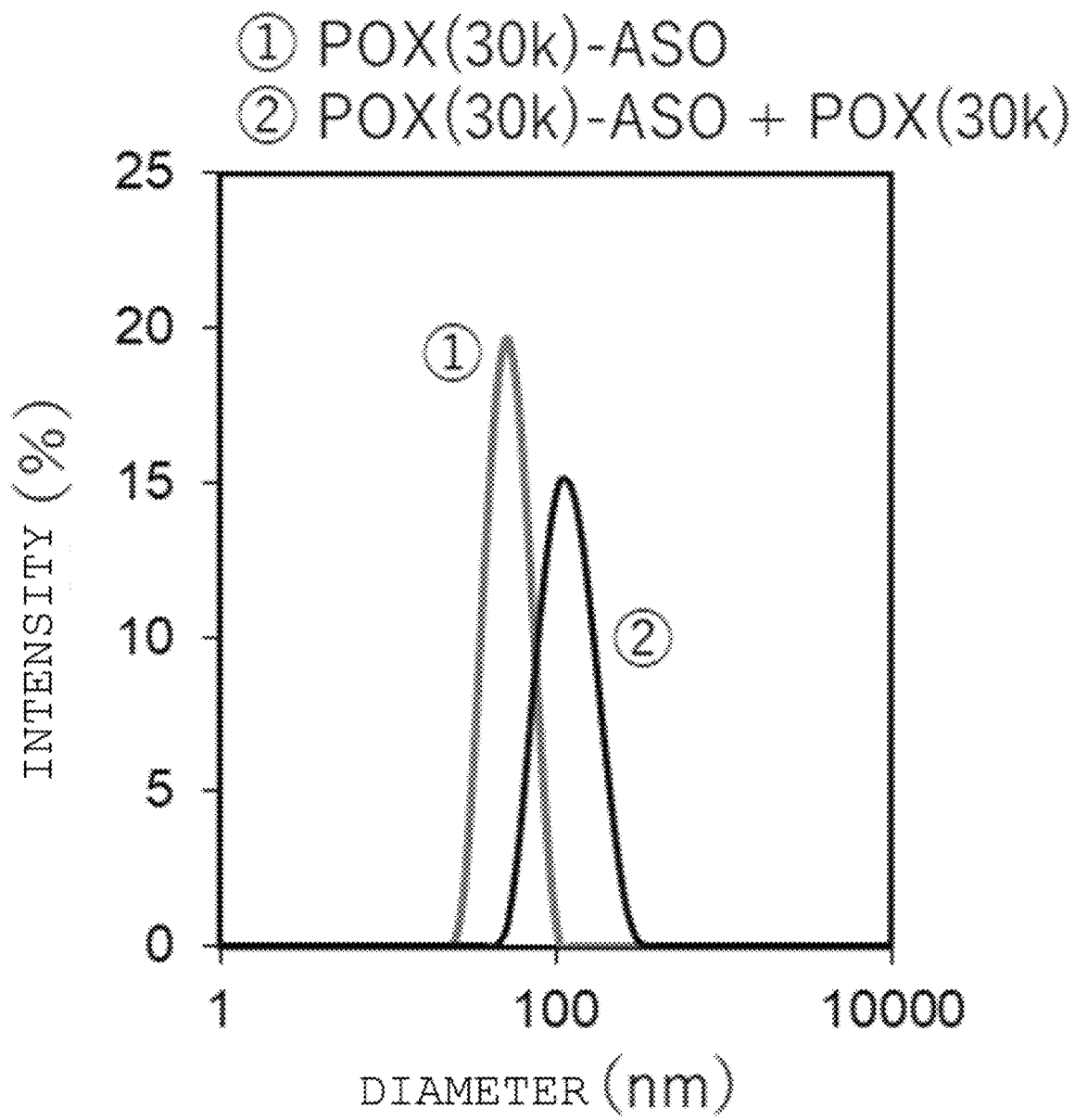
FIG. 15 includes size distribution histograms of ASOballs prepared from PDX(30k)-ASO and ASOballs prepared after the addition of PDX(30k) to PDX(30k)-ASO, determined by DLS measurement at 37° C. and an ASO concentration of 5 μM.

As shown in FIG. 15, it is found that the addition of PDX(30k) increased the size of ASOballs while maintaining a unimodal peak. In addition, the $D_H$/PDI of the ASOballs in the case of having PDX(30k) added thereto and that in the case of no addition thereof were 109 nm/0.11 and 50 nm/0.06, respectively. It is recognized from these results that the size of ASOballs can be adjusted by adding PDX having no ASO conjugated thereto to PDX-ASO.

[Biodistributions of ASOballs of Different Sizes after Intratracheal Administration]

ASOballs were each prepared from a sample containing PDX(30k)-ASO at a concentration of 20 µM (in which PDX(30k)-ASO-AF6 accounted for 10 µM), or from the same sample except for additionally containing PDX(30k) at a concentration of 20 µM, in 10 mM HEPES buffer containing 150 mM NaCl at 37° C. Intratracheal administration of the ASOballs to BALB/c mice (50 µL, about 8 µg ASO/mouse, n=3) was performed as described above. At 24 hours post-administration, the mice were sacrificed, and individual organs including liver, spleen, kidney, heart, and lung were excised. Each tissue was weighed and homogenized, and the fluorescence intensity was detected with Tecan Spark™. Results are expressed as mean and standard deviation in FIG. 16 (n=3, *p<0.05).

Figure 16:
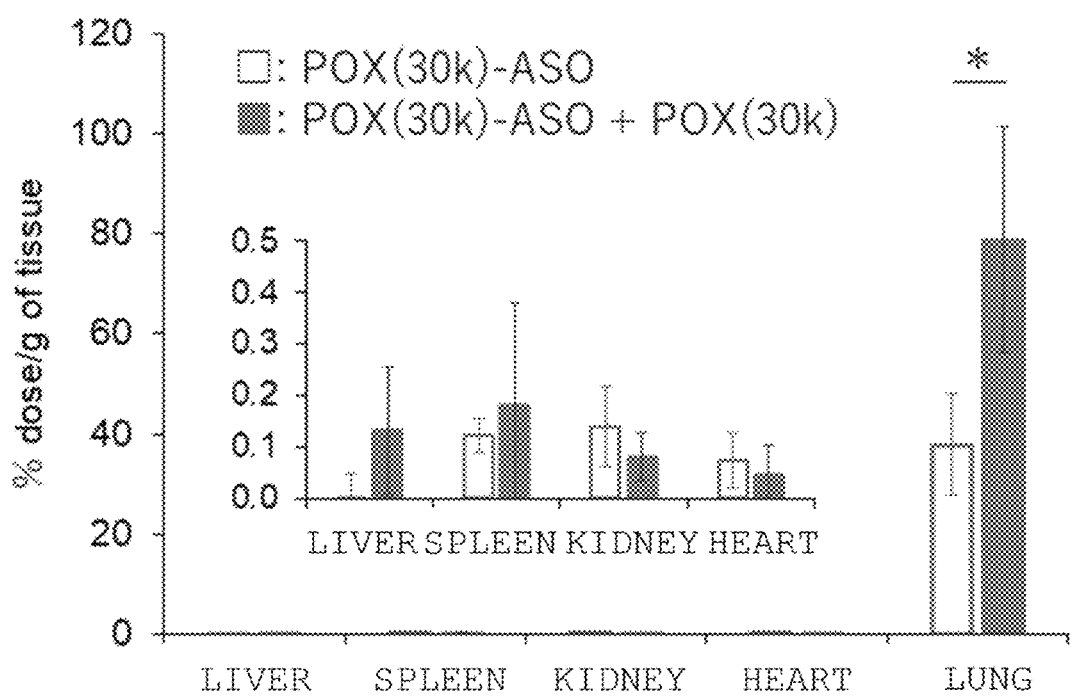
FIG. 16 is a graph showing the fluorescence intensities of homogenized organs (liver, spleen, kidney, heart, and lung) measured by a microplate reader 24 hours post-intratracheal administration. Results are expressed as mean±standard deviation (n=3; *$p<0.05$).

As shown in FIG. 16, the two kinds of ASOballs having different sizes both showed remarkably high fluorescence intensities in the lung as compared to accumulation amounts in the other organs (<0.2% dose $g^{-1}$ tissue). The accumulation amounts of the ASOballs prepared with and without the addition of PDX(30k) in the lung were 79±23% and 38±10% dose $g^{-1}$ tissue, respectively, and hence the ASOballs having the larger size showed a significantly higher lung accumulation property. This is conceivably because, with the increase in size of the ASOballs, the migration thereof into the bloodstream was more effectively suppressed.

INDUSTRIAL APPLICABILITY

The drug-polymer conjugate and the micellar aggregate thereof of the present invention can be suitably used in the field of DDSs.

The invention claimed is:

1. A drug-polymer conjugate having thermoresponsiveness, comprising:
   at least one thermoresponsive polymer segment; and
   at least one drug covalently bound to at least one end of the at least one thermoresponsive polymer segment,
   the drug-polymer conjugate having a lower critical solution temperature.

2. The drug-polymer conjugate according to claim 1, wherein the at least one thermoresponsive polymer segment has a molecular weight of $1.0 \times 10^4$ or more.

3. The drug-polymer conjugate according to claim 1, wherein the lower critical solution temperature falls within a range of from 0° C. to 35° C.

4. A micellar aggregate comprising a plurality of the drug-polymer conjugate according to claim 1, wherein the thermoresponsive polymer segments are arranged inward, and the drugs are arranged outward.

5. The micellar aggregate according to claim 4, wherein the at least one drug is a nucleic acid or a peptide.

6. The micellar aggregate according to claim 5, wherein the at least one drug is selected from the group consisting of an antisense oligonucleotide, siRNA, miRNA, a hetero nucleic acid, a CpG oligonucleotide, a nucleic acid aptamer, and a decoy nucleic acid.

7. The micellar aggregate according to claim 6, wherein the micellar aggregate has a hydrodynamic diameter of from 10 nm to 300 nm.

8. A pharmaceutical composition, comprising the micellar aggregate of claim 6.

9. The pharmaceutical composition according to claim 8, wherein the pharmaceutical composition is an inhalant.

10. A method of delivering the pharmaceutical composition of claim 8 to a lung, comprising nasally administering or intratracheally administering the pharmaceutical composition to an individual in need of intervention.

11. A method of producing a micellar aggregate, comprising:
   dissolving a plurality of the drug-polymer conjugate of claim 1 in an aqueous medium at a temperature equal to or lower than the lower critical solution temperature to obtain a drug-polymer conjugate solution; and
   subsequently heating the drug-polymer conjugate solution to a temperature higher than the lower critical solution temperature to aggregate the drug-polymer conjugates.

12. The micellar aggregate according to claim 6, wherein each of the drug-polymer conjugates has a formula selected from the group consisting of:

A-B,

B1-A-B2, and

A1-B-A2, wherein:
   A is the at least one thermoresponsive polymer segment,
   A1 is a first one of the at least one thermoresponsive polymer segment,
   A2 is a second one of the at least one thermoresponsive polymer segment,
   B is the at least one drug,
   B1 is a first one of the at least one drug, and
   B2 is a second one of the at least one drug.

13. The micellar aggregate according to claim 6, wherein the at least one thermoresponsive polymer segment comprises a poly(oxazoline)-based thermoresponsive polymer.

14. A micellar aggregate comprising a plurality of drug-polymer conjugates, wherein each of the drug-polymer conjugates comprises:
   a first thermoresponsive polymer segment having a lower critical solution temperature, wherein the at least one thermoresponsive polymer segment is hydrophilic in an aqueous medium at temperatures lower than the lower critical solution temperature and the at least one thermoresponsive polymer segment is hydrophobic in the aqueous medium at temperatures equal to or higher than the lower critical solution temperature; and
   a drug covalently bound to a first end portion of the first thermoresponsive polymer segment;
   wherein the thermoresponsive polymer segments are arranged inward in the micellar aggregate, and the drugs are arranged outward in the micellar aggregate.

15. The micellar aggregate according to claim 14, wherein:
   the first thermoresponsive polymer has a molecular weight of $1.0 \times 10^4$ or more; and
   the lower critical solution temperature is 0° C. to 35° C.

16. The micellar aggregate according to claim 15, wherein the at least one drug is a nucleic acid or a peptide.

17. The micellar aggregate according to claim 16, wherein each of the drug-polymer conjugates has a formula selected from the group consisting of:

A-B,

B1-A-B2, and

A1-B-A2, wherein:
   A and A1 are the first thermoresponsive polymer segment,
   A2 is a second thermoresponsive polymer segment,
   B and B1 are the first one drug, and
   B2 is a second drug.

18. The micellar aggregate according to claim 17, wherein the first and second thermoresponsive polymer segments each comprise a poly(oxazoline)-based thermoresponsive polymer.

19. The micellar aggregate according to claim 6, wherein the thermoresponsive polymer segments each have a molecular weight of $1.0 \times 10^4$ or more.

20. The micellar aggregate according to claim 6, wherein the lower critical solution temperature falls within a range of from 0° C. to 35° C.

* * * * *

UNITED STATES PATENT AND TRADEMARK OFFICE
CERTIFICATE OF CORRECTION

| | | |
|---|---|---|
| PATENT NO. | : 12,409,232 B2 | Page 1 of 1 |
| APPLICATION NO. | : 17/628676 | |
| DATED | : September 9, 2025 | |
| INVENTOR(S) | : Kanjiro Miyata et al. | |

It is certified that error appears in the above-identified patent and that said Letters Patent is hereby corrected as shown below:

In the Claims

In Claim 7, at Column 23, Line 26, replace "claim 6" with "claim 4".

In Claim 8, at Column 23, Line 30, replace "claim 6" with "claim 4".

In Claim 12, at Column 23, Line 46, replace "claim 6" with "claim 4".

In Claim 13, at Column 24, Line 26, replace "claim 6" with "claim 4".

Signed and Sealed this
Thirteenth Day of January, 2026

John A. Squires
*Director of the United States Patent and Trademark Office*

SEQUENCE LISTING

<160> NUMBER OF SEQ ID NOS: 6

<210> SEQ ID NO 1
<211> LENGTH: 21
<212> TYPE: DNA

<213> ORGANISM: Artificial Sequence
<220> FEATURE:
<223> OTHER INFORMATION: taurine upregulated gene 1 (TUG1) long
      non-coding RNA (lncRNA)-targeted antisense oligonucleotide

<400> SEQUENCE: 1
tgaatttcaa tcatttgaga t                                          21

<210> SEQ ID NO 2
<211> LENGTH: 21
<212> TYPE: DNA
<213> ORGANISM: Artificial Sequence
<220> FEATURE:
<223> OTHER INFORMATION: GL3 luciferase-targeted antisense
      oligonucleotide

<400> SEQUENCE: 2
tcgaagtact cagcgtaagt t                                          21

<210> SEQ ID NO 3
<211> LENGTH: 18
<212> TYPE: DNA
<213> ORGANISM: Artificial Sequence
<220> FEATURE:
<223> OTHER INFORMATION: Primer sequence for GAPDH:forward

<400> SEQUENCE: 3
ccacccatgg caaattcc                                              18

<210> SEQ ID NO 4
<211> LENGTH: 20
<212> TYPE: DNA
<213> ORGANISM: Artificial Sequence
<220> FEATURE:
<223> OTHER INFORMATION: Primer sequence for GAPDH:reverse

<400> SEQUENCE: 4
caggaggcat tgctgatgat                                            20

<210> SEQ ID NO 5
<211> LENGTH: 24
<212> TYPE: DNA
<213> ORGANISM: Artificial Sequence
<220> FEATURE:
<223> OTHER INFORMATION: Primer sequence for TUG1:forward

<400> SEQUENCE: 5
aggtagaacc tctatgcatt ttgt                                       24

<210> SEQ ID NO 6
<211> LENGTH: 25
<212> TYPE: DNA
<213> ORGANISM: Artificial Sequence
<220> FEATURE:
<223> OTHER INFORMATION: Primer sequence for TUG1:reverse

<400> SEQUENCE: 6
actcttgctt cactacttca tccag                                      25